United States Patent
Nandy et al.

(10) Patent No.: US 11,414,366 B2
(45) Date of Patent: Aug. 16, 2022

(54) SERIES OF COMPOUNDS FOR TREATMENT OF SKIN DISEASES AND OTHER CONDITIONS

(71) Applicant: Unigen, Inc., Tacoma, WA (US)

(72) Inventors: Sandip K. Nandy, Olympia, WA (US); Teresa Horm, Renton, WA (US); Kelly Rose Dawkins, Tacoma, WA (US)

(73) Assignee: Unigen, Inc., Tacoma, WA (US)

( * ) Notice: Subject to any disclaimer, the term of this patent is extended or adjusted under 35 U.S.C. 154(b) by 100 days.

(21) Appl. No.: 16/600,536

(22) Filed: Oct. 13, 2019

(65) Prior Publication Data

US 2020/0115307 A1 Apr. 16, 2020

Related U.S. Application Data

(60) Provisional application No. 62/745,380, filed on Oct. 14, 2018.

(51) Int. Cl.
| | |
|---|---|
| *C07C 39/20* | (2006.01) |
| *A61P 17/10* | (2006.01) |
| *A61P 31/04* | (2006.01) |
| *A61P 29/00* | (2006.01) |
| *A61P 35/00* | (2006.01) |
| *A23B 7/154* | (2006.01) |
| *A23L 3/349* | (2006.01) |
| *C07C 59/54* | (2006.01) |
| *C07C 233/91* | (2006.01) |
| *C07D 213/16* | (2006.01) |
| *C07D 213/30* | (2006.01) |

(52) U.S. Cl.
CPC ............... *C07C 39/20* (2013.01); *A23B 7/154* (2013.01); *A23L 3/349* (2013.01); *A61P 17/10* (2018.01); *A61P 29/00* (2018.01); *A61P 31/04* (2018.01); *A61P 35/00* (2018.01); *C07C 59/54* (2013.01); *C07C 233/91* (2013.01); *C07D 213/16* (2013.01); *C07D 213/30* (2013.01); *A23V 2002/00* (2013.01); *C07B 2200/09* (2013.01)

(58) Field of Classification Search
None
See application file for complete search history.

(56) References Cited

U.S. PATENT DOCUMENTS

| | | | | |
|---|---|---|---|---|
| 8,362,305 | B2 * | 1/2013 | Nandy | C07C 39/15 568/744 |
| 8,658,838 | B2 * | 2/2014 | Nandy | A61P 31/04 568/744 |
| 9,096,507 | B2 * | 8/2015 | Nandy | C07D 317/54 |
| 9,682,910 | B2 * | 6/2017 | Nandy | A23L 3/3481 |

OTHER PUBLICATIONS

Rong et al., Organic Letters (2018), 20(19), pp. 6289-6293.*

* cited by examiner

*Primary Examiner* — Brian J Davis
(74) *Attorney, Agent, or Firm* — Sandra Poteat Thompson; Finlayson Toffer Roosevelt & Lilly LLP

(57) ABSTRACT

Compounds and methods related to the prevention and treatment of diseases and conditions, some of which are facilitated by melanogenesis are disclosed. Specifically, the present subject matter includes a series of compounds and compositions and their use for anti-melanogenic and anti-oxidant activity. This subject matter also includes the treatment of skin disorder due to acne vulgaris and related inflammatory and post inflammatory hyperpigmentation. Methods for synthesizing contemplated compounds are also disclosed.

14 Claims, 12 Drawing Sheets

80% propylene glycol, 0.5% DMSO 0.025%

0.05%

12

80% propylene glycol, 0.5% DMSO 0.025%

0.05%

15

SERIES OF COMPOUNDS FOR TREATMENT OF SKIN DISEASES AND OTHER CONDITIONS

This United States Utility Application claims priority to U.S. Provisional Application Ser. No. 62/745,380 entitled "A Series of Novel Compounds for Treatment of Acne Vulgaris, Inflammation, and Skin Disorders", which was filed on Oct. 14, 2018, which is commonly-owned and which is incorporated by reference in its entirety.

FIELD OF THE SUBJECT MATTER

This subject matter generally relates to the prevention and treatment of diseases and conditions, some of which are facilitated by melanogenesis. Specifically, the present subject matter includes a series of compounds and compositions and their use for anti-melanogenic and antioxidant activity. This subject matter also includes the treatment of skin disorder due to acne vulgaris and related inflammatory and post inflammatory hyperpigmentation. Further included in the present subject matter are methods for synthesizing these compounds.

BACKGROUND

There is a great demand for materials able to inhibit or prevent excessive pigmentation of the skin. Melanin, the skin's natural pigment, is a nitrogenous polymer synthesized in melanosomes, which are membrane-bound organelle present within melanocytes. Melanin is produced in varying concentrations, depending on skin type (genetic disposition) and environmental conditions. Melanocytes are melanin producing cells that occur in the basal membrane of the epidermis, hair follicles, eyes, inner ear, bones, heart and brain of humans. When stimulated, by factors such as ultraviolet (UV) light melanocytes divide more rapidly, thereby producing greater quantities of melanin. The melanin is then transported in mature melanosomes to keratinocytes, within the epidermis where it becomes visible as a skin color varying from brown to black (eumelanin) and red to yellow (pheomelanin) (Prota G. *Med. Res. Rev.* 1988, 8, 525-556). In human skin, melanin is believed to act as a protective agent against ultraviolet radiation. As such, people living close to equator have darker skin than those living in areas away from the equator. Overproduction of melanin can cause different types of abnormal skin color, hair color, and other dermatological disorders, such as melasma, age spots and sites of actinic damage (Seiberg et al. (2000) J. Invest. Dermatol. 115:162; Paine et al. (2001) J. Invest. Dermatol. 116:587).

Modulators of melanogenesis (the production of melanin) may be designed or chosen to function in a variety of ways as illustrated in Prior Art FIG. 1. With reference to Prior Art FIG. 1, the two types of melanin, eumelanin and pheomelanin are synthesized in response to external signals which activate signaling cascades and result in the activation of the MITF transcription factor and the production of downstream gene products, including enzymes which are directly involved in melanogenesis. Activation of the PKC (brown), cAMP (blue), MEK (purple), or WNT (orange) pathways by ligand binding through KIT, MC1R, or other receptors at the melanocyte cell surface drives activation of MITF. Upregulation of melanogenesis-related genes enable production of melanin in the melanosome, a membrane-bound vesicle.

Melanin is produced from precursors by the tyrosinase enzyme for which there is a strict requirement. Human tyrosinase has two distinct activities: tyrosine hydroxylation, which catalyzes the conversion of tyrosine to L-DOPA, and DOPA oxidation, which catalyzes the conversion of L-DOPA to dopaquinone. Both steps are required for eumelanin production from tyrosine. Phenylalanine hydroxylase catalyzes the production of tyrosine from phenylalanine, if additional tyrosine substrate is required. Additional enzymes, Tyrosinase-related protein 1 (TRP1) and Tyrosinase-related protein 2 (TRP2), carry out the conversions of downstream effectors to eumelanin.

In melanocytes, regulation of melanogenesis occurs at several levels. Tyrosinase and other melanogenesis-related proteins, such as TRP1 and PMEL17, premelanosome protein 17, are regulated at the gene expression level by MITF, the microphthalmia-associated transcription factor. Activation of MITF increases expression of these genes and consequently, increases melanin production. Activation status of MITF is regulated by downstream kinases from the cAMP, MEK, PI3K, and Wnt pathways, which are regulated at the cell surface by ligands binding to receptors. Kit receptor is activated by its ligand, SCF, stem cell factor, and MC1R is activated by either α-MSH, alpha melanocyte stimulating hormone, or ACTH, adrenocorticotropic hormone. Ligand binding at these receptors, or others involved in these signaling cascades, results in activation of kinase signaling pathways and downstream activation of MITF, upregulation of melanogenic genes, and production of melanin.

There is also a structural component to melanogenesis regulation. Within melanosomes themselves, the reactions in the melanogenic pathway largely occur on scaffolds of PMEL17, a glycoprotein that binds melanin intermediate products and allows for targeted catalysis by melanogenic enzymes, tyrosinase, TRP1, and TRP2. PMEL17 is itself a membrane-bound glycoprotein until it is processed within the melanosome into a soluble protein by BACE-2, Beta-site APP Cleaving Enzyme-2, γ-secretase, pro-protein convertase, and metalloproteinase. Once soluble, PMEL17 forms fibrils which sequester melanin precursors to allow for increased access by catalytic enzymes. MART-1, Melanoma-associated antigen recognized by T-cells, or Melan-A, interacts with PMEL17 and is critical for PMEL17 expression and function.

Melanosomes containing mature melanin are transported from melanocytes to keratinocytes to disperse pigment throughout the skin tissue. This occurs due to clathrin-coated vesicle transport machinery, including Rab G-proteins, SNAREs, and clathrin coat proteins. Uptake by the keratinocytes requires PAR-2.

Disruption of melanogenesis occurs through the disruption of melanin production itself through inhibition of one of the melanogenic enzymes, inhibition of enzyme production, increased degradation of enzymes, inhibition of structural scaffolds affiliated with melanogenesis or melanosome biosynthesis, or inhibition of melanosome transport. The compounds included in this subject matter are anti-melanogenic due to disruption of melanogenesis through one or more of these mechanisms.

This subject matter also includes the treatment of skin disorder due to acne vulgaris and related inflammatory and post inflammatory hyperpigmentation. Acne vulgaris is multifactorial disease, involving hyperkeratinization, hormonal function, bacterial proliferation, and immune hypersensitivity. It is common and affects nearly all teenagers and adults at some time in their lives. Acne generally occurs within the hair follicle. At the base of hair follicle, sebaceous glands are situated which produces sebum. In a healthy skin, the sebaceous gland produces the appropriate amount of sebum to maintain the health of the surrounding skin, and the sebum is efficiently extruded along with the hair. However, excessive growth of the sebaceous glands (sebaceous hyperplasia) and overproduction of sebum can be an important contributor to acne symptoms. Sebaceous hyperplasia can be triggered by increases in androgen hormones which tends to peak in the mid-teenage years and is considered a prime factor in initiating acne. The androgenic hormones (sex hormones) are secreted in the body and enter into the sebaceous gland, where the enzyme 5-alpha reductase converts the testosterone into di-hydrotestosterone; this in turn stimulates sebum formation in the sebaceous glands.

As a result of hyperactivity of sebaceous gland, excess sebum mixed with dried skin that clogged the follicle. When pores are clogged, acne bacteria have a way of "breaking out" of the pore so their descendants can go to live in another pore. They release chemicals that sensitize skin cells to the immune system.

Many of the components made by the bacteria are easily recognized by the immune system as "foreign" molecules which induce immune cells to secrete several proinflammatory cytokines, such as TNF-$\alpha$, (IL)-8, and IL-1$\beta$, and activate inflammatory pathways involving the activity of enzymes such as COX-1, COX-2, 5-LOX, that are important for the development of skin inflammation.

When the immune system attacks the bacteria, it also kills healthy skin cells. This reddens and inflames the skin, and at some point, some bacteria will escape when the pimple bursts open. While the breakout is still healing, these spots might start off as purple or red before fading into a darker tone of the surrounding skin. Post inflammatory hyperpigmentation (PIH) is a unique skin pigmentation condition that involves increased melanin synthesis and deposition. Human skin contains specialized cells, called melanocytes, which are located at the base of the epidermis. These cells are programmed to manufacture a pigment, called melanin, in response to damage and in an attempt to protect or heal itself. PIH is also characterized by apoptosis of melanocyte cells due to oxidative stress and assaults from mediators and cytokines of inflammatory and immune responses. The melanin deposition (i.e., hyperpigmentation) occurs beyond the epidermal level, with significant melanin being released into the papillary dermis and trapped by large immune cells. These unique histological characteristics of PIH present a number of difficulties for treatment with traditional agents.

Topical antimicrobials, including benzoyl peroxide and antibiotics, are effective in treating inflammatory disease. Benzoyl peroxide is a bactericidal agent that prevents the resistance of *P. acnes* to antibiotic therapy and has moderate comedolytic and anti-inflammatory properties. It is available in various topical preparations, ranging in strength from 2.5% to 10.0%. Any strength can be used initially, although it may be more prudent to start with a lower concentration; stronger preparations are more irritating and not necessarily more effective. Benzoyl peroxide kills *P. acnes* by releasing oxygen within the follicle. It can be fast-acting, with a response as early as five days. The main drawback is that it is a potent bleaching agent. Patients should be warned that fabrics that come in contact with benzoyl peroxide, including towels, bed sheets and clothing, may be bleached.

Topical erythromycin and clindamycin are generally well-tolerated and have been shown to reduce inflammatory lesions by 46% to 70% in several randomized controlled trials. Monotherapy with topical antibiotics should not be used routinely because *P. acnes* may become resistant within one month after daily treatment has begun. Some argue that this resistance is not relevant because the antibiotics (e.g., clindamycin, tetracyclines, erythromycin) also have intrinsic anti-inflammatory and antimicrobial effects. However, antibiotic-resistant *Staphylococcus epidermidis* and *Staphylococcus aureus* may also develop with monotherapy; resistance can be avoided when a topical antibiotic is combined with benzoyl peroxide. Combination therapy, for example with retinoids and antibiotics, is more effective than either agent used alone. However, the agents should be applied at separate times, unless they are known to be compatible. Benzoyl peroxide may oxidize retinoids, such as tretinoin, if applied simultaneously. A 12-week randomized controlled trial involving 249 patients with mild to moderate acne showed treatment with adapalene gel 0.1% and clindamycin 1.0% to be superior to that with clindamycin 1.0% used alone. If inflammatory lesions are present, topical antibiotics containing benzoyl peroxide should be combined with a topical retinoid (e.g., topical antibiotic with benzoyl peroxide in the morning and retinoid at night). A review of three clinical studies with 1259 patients showed that a combination of clindamycin 1% and benzoyl peroxide 5% was more effective than either drug used alone in reducing lesions and suppressing *P. acnes*.

Common treatments for PIH are focused on prevention of further pigment development by controlling inflammation with corticosteroids and using photoprotection agents. Chemical peeling compounds, such as salicylic acid and glycolic acid, are also used to facilitate the skin renewal function and to remove or diminish the pigmentation. Topical retinoids have also been used to treat PIH, but such methods require up to 40 weeks before significant benefits are seen.

Tyrosinase inhibitors, or skin whiteners, such as hydroquinone, azelaic acid, kojic acid and licorice extract, have also been employed for treatment of PIH. One significant disadvantage of using traditional skin whitening agents or tyrosinase inhibitors is the non-specific discoloration of the regular skin near the PIH site. This effect reduces the color of the background skin and makes the PIH sites more prominent. Thus, these agents must be applied very carefully over the site of the PIH. In addition, tyrosinase inhibitors are only effective for epidermal hyperpigmentation since this is the location of melanin synthesis by tyrosinase. Because post inflammatory pigmentation is in a deep layer of the skin (e.g., papillary dermis), it takes more than 6 months of continued application of hydroquinone medication before visual changes of the dark marks are seen. Finally, hydroquinone type skin whiteners or tyrosinase inhibitors are associated with side effects including skin irritation, dryness, teratogenicity and induction of vitilago and skin cancers.

Post inflammatory hyperpigmentation can be derived from endogenous inflammatory skin disorders such as acne, atopic dermatitis, allergic contact dermatitis, incontinent pigmentation, lichen planus, lupus erythematosus, or morphea. Other causes of PIH include exogenous inflammatory stimuli such as mechanical trauma, ionizing and nonionizing radiation, burns, laser therapies and skin infections. Current therapeutic agents for the above skin disorders are ineffective for preventing, alleviating, reducing or treating PIH. For example, the above skin disorders are often treated with anti-inflammatory agents, such as retinoids, COX inhibitors (e.g., salicylic acid), nonsteroidal anti-inflammatory drugs (NSAIDs), antimicrobial agents or hormonal drugs, but these treatments have been shown to be ineffective against PIH.

While significant advances have been made in the field of skin care and many compounds have been reported from natural as well as synthetic sources as potent tyrosinase inhibitors with anti-melanogenic activity, very few of them have shown to be effective skin whiteners. Most of these agents were found either toxic or shown to have adverse side effects in humans. Additionally, many compounds have been reported as strong anti-melanogenic or antimicrobial or anti-inflammatory to inhibit PIH, none of them has quadruple actions. As such, there continues to be a need in the art for methods for preventing, alleviating, reducing or treating melanogenic, acne vulgaris, inflammation and excess pigmentation having a single compound possess quadruple actions. The present subject matter fulfills these needs and provides further related advantages.

SUMMARY OF THE SUBJECT MATTER

Compounds of formula I are described herein:

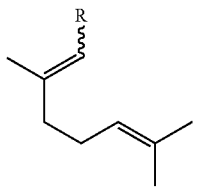

Formula I wherein R comprises an aromatic or heteroaromatic ring selected from the group consisting of phenyl, naphthyl, biphenyl, 2-pyridyl, 3-pyridyl, 4-pyridyl, 2-furanyl, 3-furanyl; wherein R is substituted with 1 to 3 moieties (R', R", R''') independently selected from the group consisting of a $C_1$-$C_{10}$ alkyl group, a $C_1$-$C_{10}$ alkoxy group or a hydroxyl group.

Compounds of formula II are described herein:

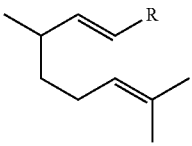

Formula II wherein R comprises an aromatic or heteroaromatic ring selected from the group consisting of phenyl, naphthyl, biphenyl, 2-pyridyl, 3-pyridyl, 4-pyridyl, 2-furanyl, 3-furanyl; wherein R is substituted with 1 to 3 moieties (R', R", R''') independently selected from the group consisting of a $C_1$-$C_{10}$ alkyl group, a $C_1$-$C_{10}$ alkoxy group or a hydroxyl group.

Compounds of formula III are described herein:

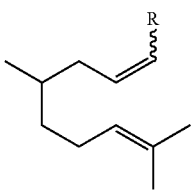

Formula III wherein R comprises an aromatic or heteroaromatic ring selected from the group consisting of phenyl, naphthyl, biphenyl, 2-pyridyl, 3-pyridyl, 4-pyridyl, 2-furanyl, 3-furanyl; wherein R is substituted with 1 to 3 moieties (R', R", R''') independently selected from the group consisting of a $C_1$-$C_{10}$ alkyl group, a $C_1$-$C_{10}$ alkoxy group or a hydroxyl group.

Compositions comprising (E/Z)-4-(2,6-dimethylhepta-1,5-dienyl)phenol (1); (E/Z)-3-(2,6-dimethylhepta-1,5-dienyl) phenol (2); (E/Z)-4-(2,6-dimethylhepta-1,5-dienyl)benzene-1,3-diol (3); (E/Z)-5-(2,6-dimethylhepta-1,5-dienyl) benzene-1,3-diol (4); (E)-4-(3,7-dimethylocta-1,6-dienyl) phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy) acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy) diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy)diacetic acid (17) or a pharmaceutically acceptable salt thereof are disclosed herein alone or in combination with one another.

Methods for inhibiting the production of melanin are disclosed comprising administering to a subject in need thereof a composition comprising at least one of the following compounds: (E/Z)-4-(2,6-dimethylhepta-1,5-dienyl) phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3, 7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing and treating diseases and conditions related to the overproduction or uneven distribution of melanin comprising administering to a subject in need thereof an effective amount of a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy) diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7- dimethylocta-1,6-dienyl) pyridine (13); (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for whitening and/or lightening skin comprising administering to a subject in need thereof a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13); (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing melanin synthesis wherein the symptom, condition, disorder, or disease associated tyrosinase inhibition comprising administering to a subject in need thereof an effective amount of a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13); (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing melanin synthesis wherein the symptom, condition, disorder, or disease associated non-tyrosinase inhibition comprising administering to a subject in need thereof an effective amount of a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13); (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing and treating diseases wherein the symptom, condition, disorder, or disease associated with free radicals, oxidative stress, UV rays induced skin damages, skin aging, skin inflammatory diseases or disorders, skin degenerative diseases or disorders comprising administering to a subject in need thereof an effective amount of a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy) acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy) diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy)diacetic acid (17) or a pharmaceutically acceptable salt thereof.

Methods for inhibit the browning and color changes in fruits, vegetables, juices and other food products comprising administering a compound are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy) diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for suppressing the activity of *Propionibacterium* (p-acnes) comprising administering to a patient in need thereof a composition are disclosed herein comprising at least one the following compounds: (E/Z)-4-(2,6-dimethyl-hepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl)benzene-1,3-diol (6); (E)-5-(3,7-dimethylocta-1,6-dienyl)benzene-1,3-diol (7); E)-6-(3,7-dimethylocta-1,6-dienyl)naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl)pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy)diacetic acid (17) or a pharmaceutically acceptable salt thereof.

Methods for deactivating the activity of proinflammatory cytokines, such as COX-1, COX-2, and 5-LOX comprising administering to a patient in need thereof a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

BRIEF DESCRIPTION OF THE FIGURES

Prior Art

FIG. 2 also illustrates graphically cell viability at varying concentrations of compound 1. The $LD_{50}$ for compound 1 was determined to be 269 μM.

FIG. 3 also illustrates graphically cell viability ($LD_{50}$) at varying concentrations of compound 4. The $LD_{50}$ for compound 15 was determined to be 127 μM.

FIG. 4 also illustrates graphically cell viability ($LD_{50}$) at varying concentrations of compound 6. The $LD_{50}$ for compound 6 was determined to be 233 μM.

FIG. 5 also illustrates graphically cell viability ($LD_{50}$) at varying concentrations of compound 7. The $LD_{50}$ for compound 7 was determined to be 152 μM.

FIG. 6 also illustrates graphically cell viability ($LD_{50}$) at varying concentrations of compound 8. The $LD_{50}$ for compound 8 was determined to be 68 μM.

FIG. 7 also illustrates graphically cell viability ($LD_{50}$) at varying concentrations of compound 12. The $LD_{50}$ for compound 12 was determined to be 385 μM.

FIG. 8 also illustrates graphically cell viability ($LD_{50}$) at varying concentrations of compound 15. The $LD_{50}$ for compound 15 was determined to be 145 μM.

DETAILED DESCRIPTION

Figure 1:
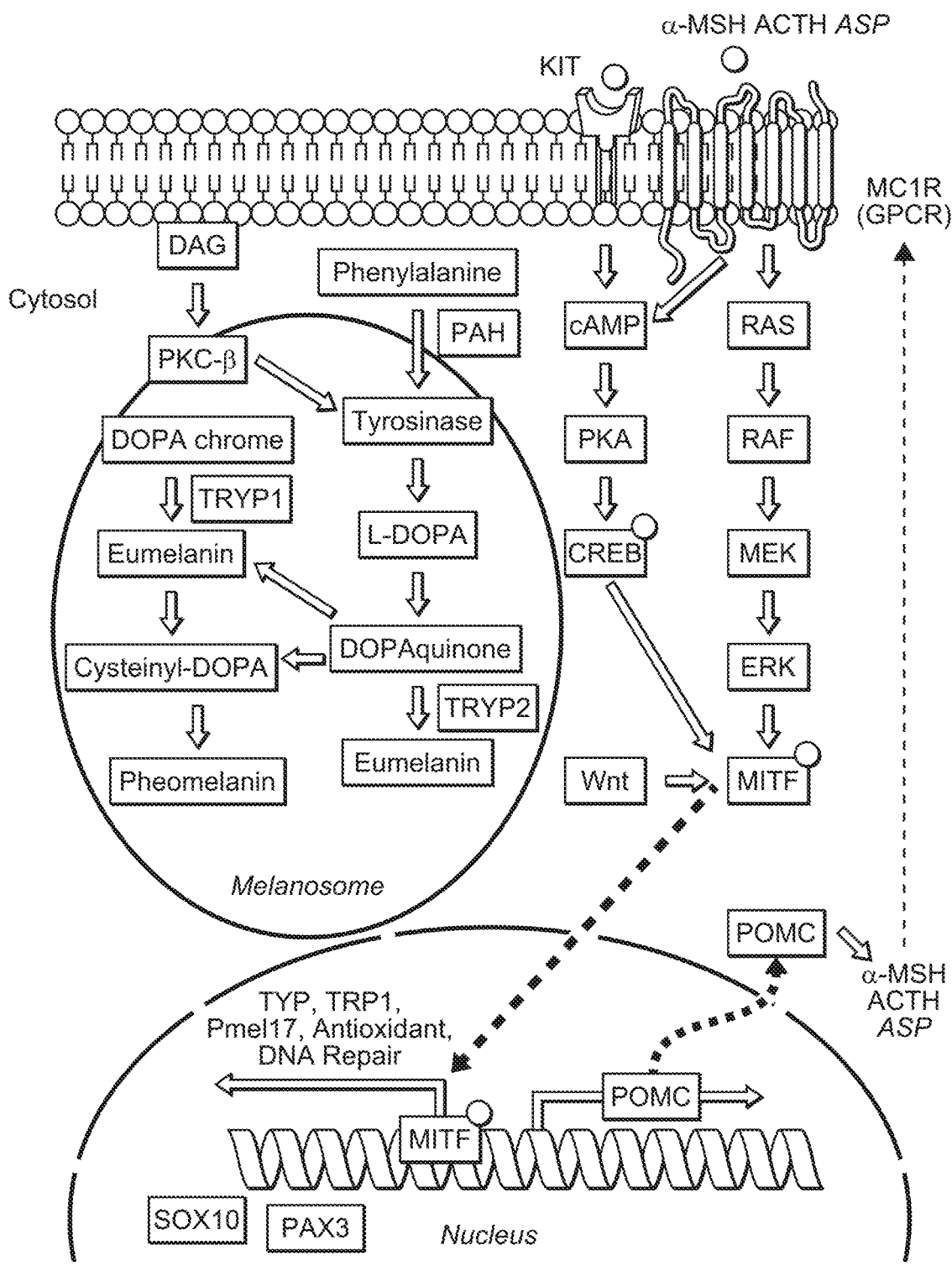
FIG. 1 shows that the two types of melanin, eumelanin and pheomelanin, are synthesized in response to external signals which activate signaling cascades and result in the activation of the MITF transcription factor and the production of downstream gene products, including enzymes which are directly involved in melanogenesis. Activation of the PKC (brown), cAMP (blue), MEK (purple), or WNT (orange) pathways by ligand binding through KIT, MC1R, or other receptors at the melanocyte cell surface drives activation of MITF. Upregulation of melanogenesis-related genes enable production of melanin in the melanosome, a membrane-bound vesicle. Melanin is produced from precursors by the tyrosinase enzyme for which there is a strict requirement.
Figure 2:
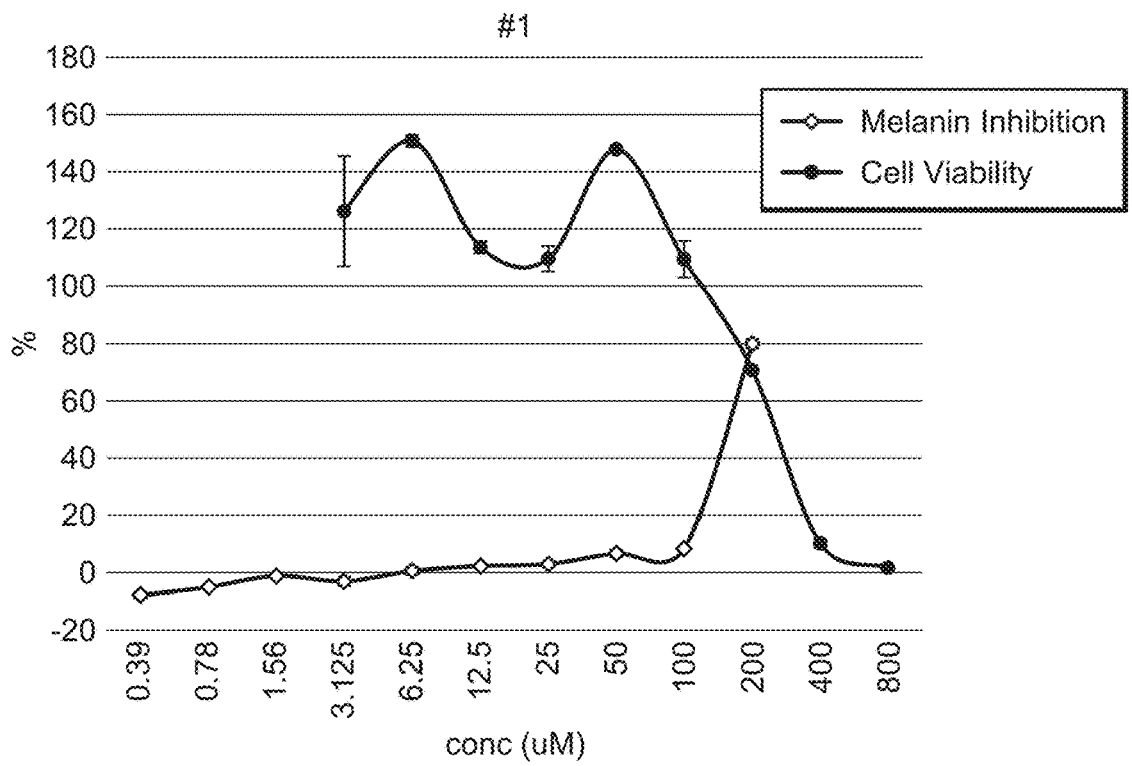
FIG. 2 illustrates graphically a profile of the inhibition in the production of melanin by (E/Z)-4-(2,6-Dimethylhepta-1,5-dienyl)phenol (1) as described in Example 5. The data is presented as melanin content (% of untreated control) vs. inhibitor concentration (μM). The IC50 of compound 1 was determined to be 158 μM.
Figure 3:
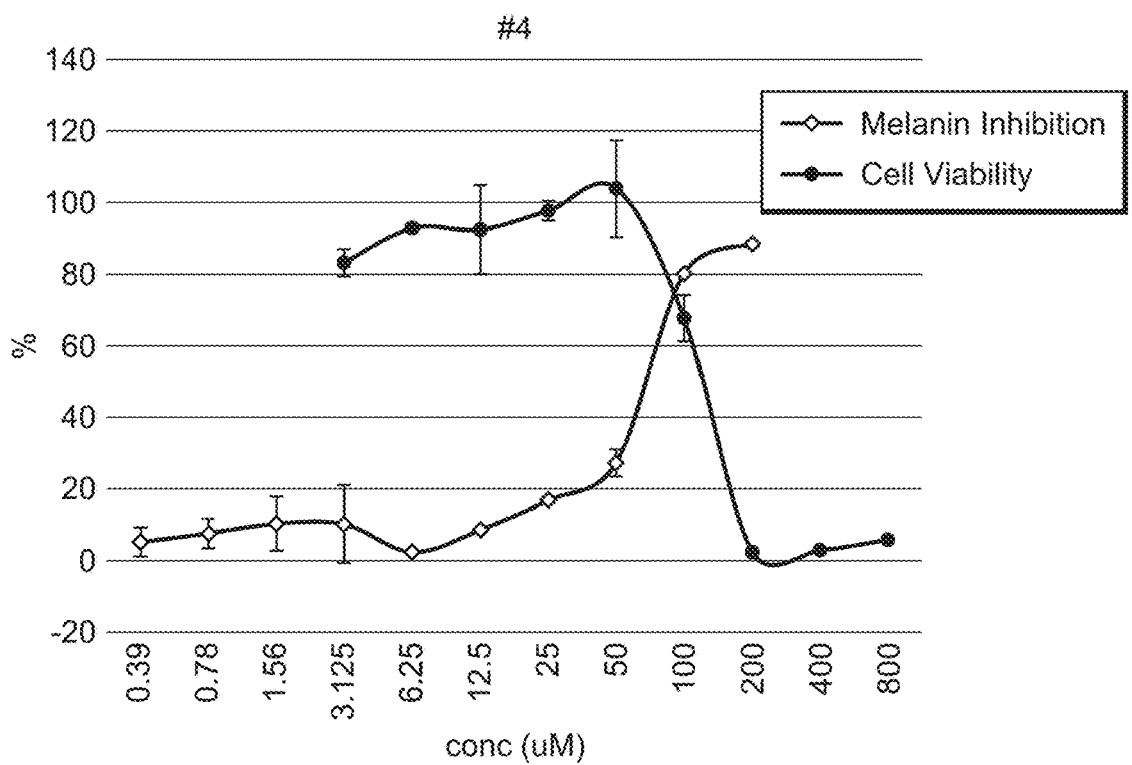
FIG. 3 illustrates graphically a profile of the inhibition in the production of melanin by (E/Z)-5-(2,6-Dimethylhepta-1,5-dienyl)benzene-1,3-diol (4) as described in Example 5. The data is presented as melanin content (% of untreated control) vs. inhibitor concentration (μM). The $IC_{50}$ of compound 4 was determined to be 72 ρM.
Figure 4:
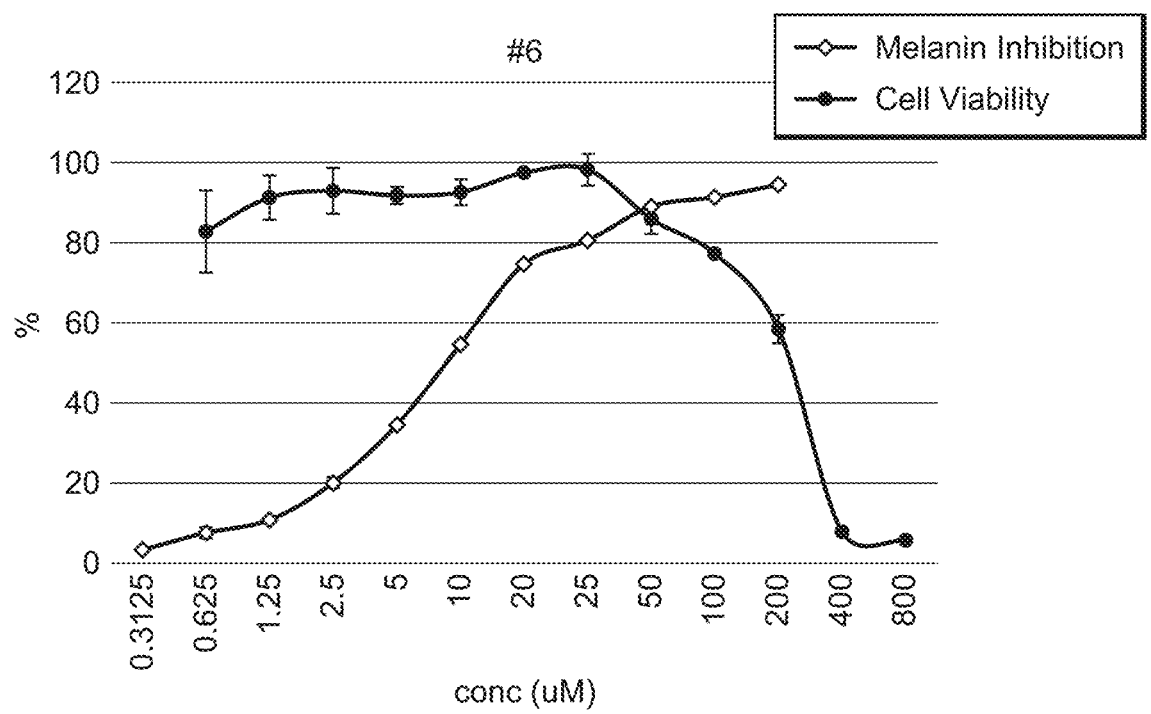
FIG. 4 illustrates graphically a profile of the inhibition in the production of melanin by (E)-4-(3,7-Dimethylocta-1,6-dienyl) benzene-1,3-diol (6) as described in Example 5. The data is presented as melanin content (% of untreated control) vs. inhibitor concentration (μM). The $IC_{50}$ of compound 6 was determined to be 9 μM.
Figure 5:
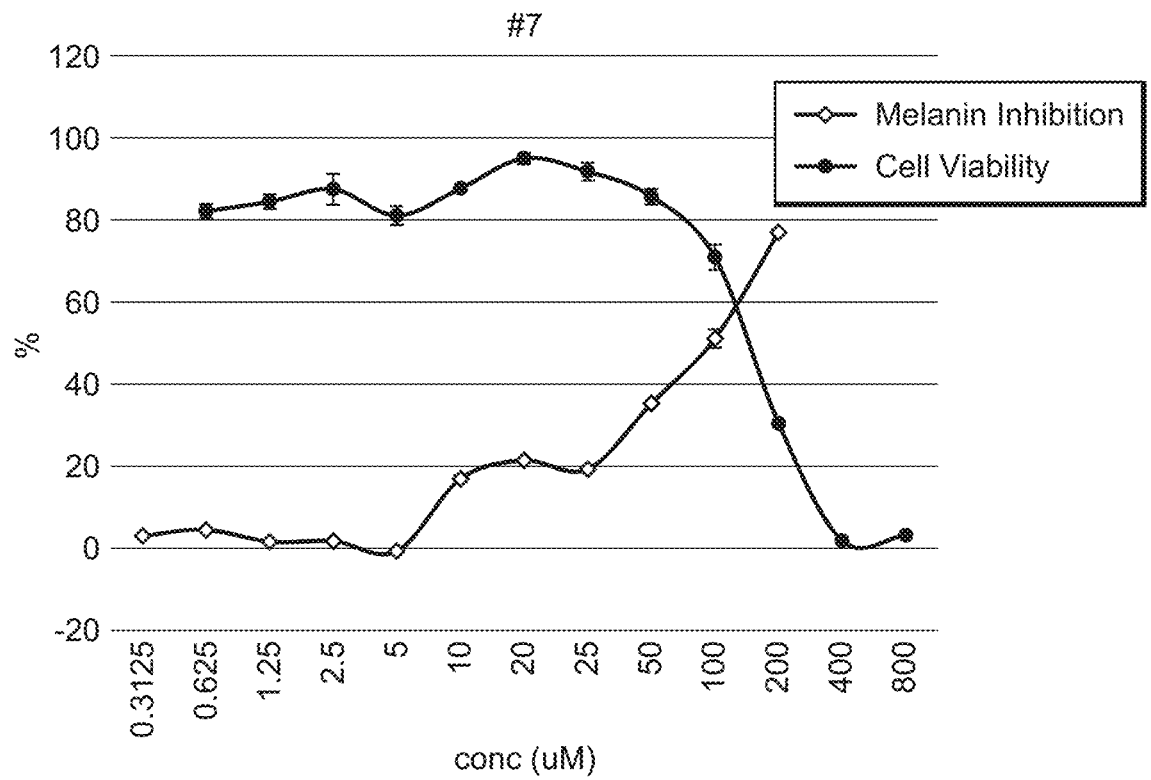
FIG. 5 illustrates graphically a profile of the inhibition in the production of melanin by (E)-5-(3,7-Dimethylocta-1,6-dienyl) benzene-1,3-diol (7) as described in Example 5. The data is presented as melanin content (% of untreated control) vs. inhibitor concentration (μM). The $IC_{50}$ of compound 7 was determined to be 97 μM.
Figure 6:
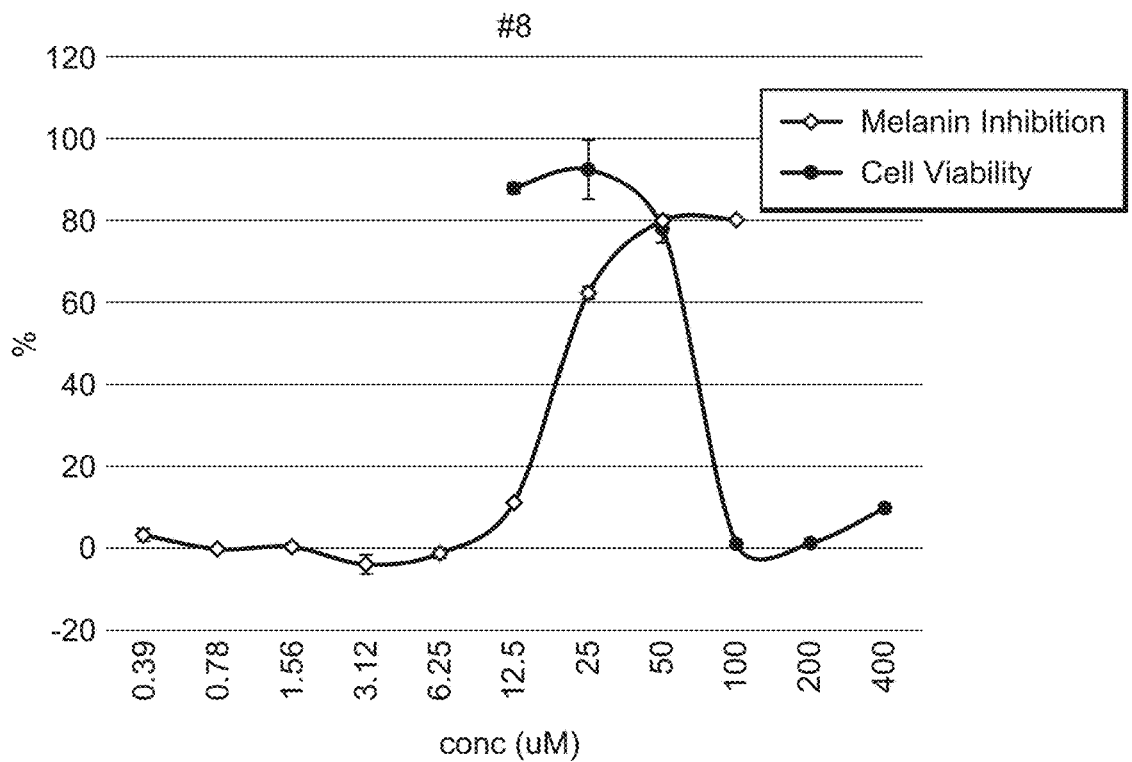
FIG. 6 illustrates graphically a profile of the inhibition in the production of melanin by (E)-6-(3,7-Dimethylocta-1,6-dienyl) naphthalene-2-ol (8) as described in Example 5. The data is presented as melanin content (% of untreated control) vs. inhibitor concentration (μM). The $IC_{50}$ of compound 8 was determined to be 22 μM.
Figure 7:
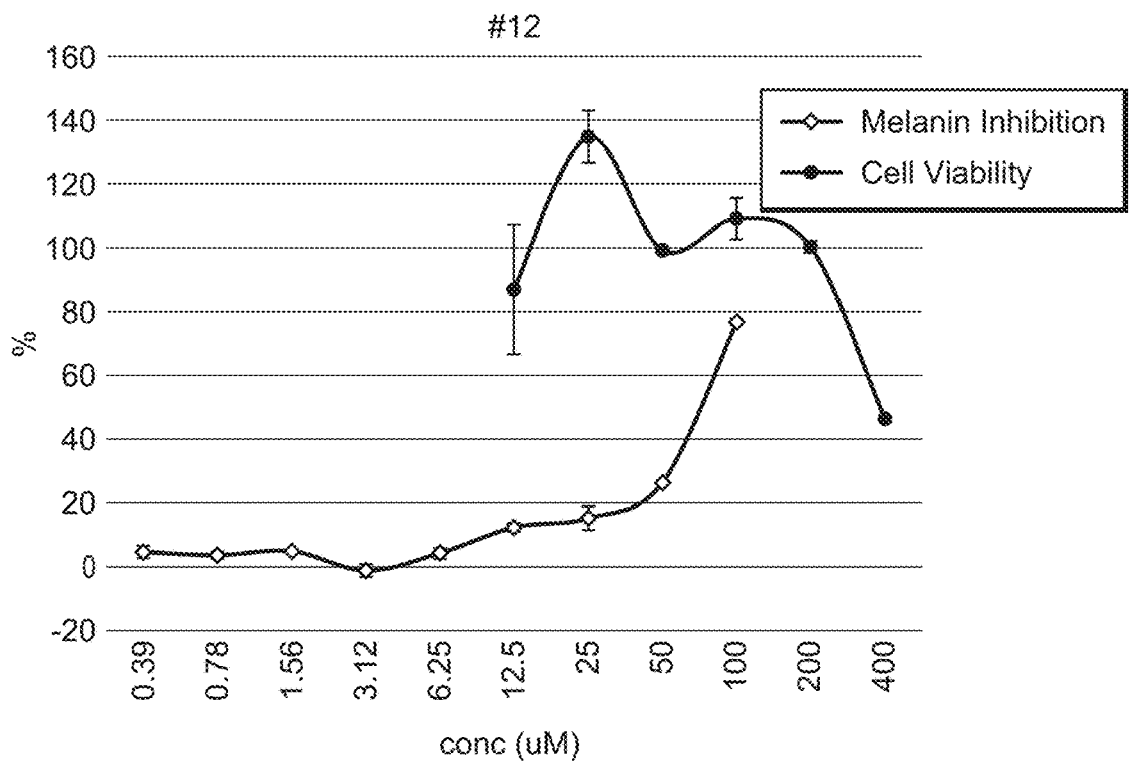
FIG. 7 illustrates graphically a profile of the inhibition in the production of melanin by (E)-3-(3,7-Dimethylocta-1,6-dienyl) pyridine (12) as described in Example 5. The data is presented as melanin content (% of untreated control) vs. inhibitor concentration (μM). The $IC_{50}$ of compound 12 was determined to be 74 μM.
Figure 8:
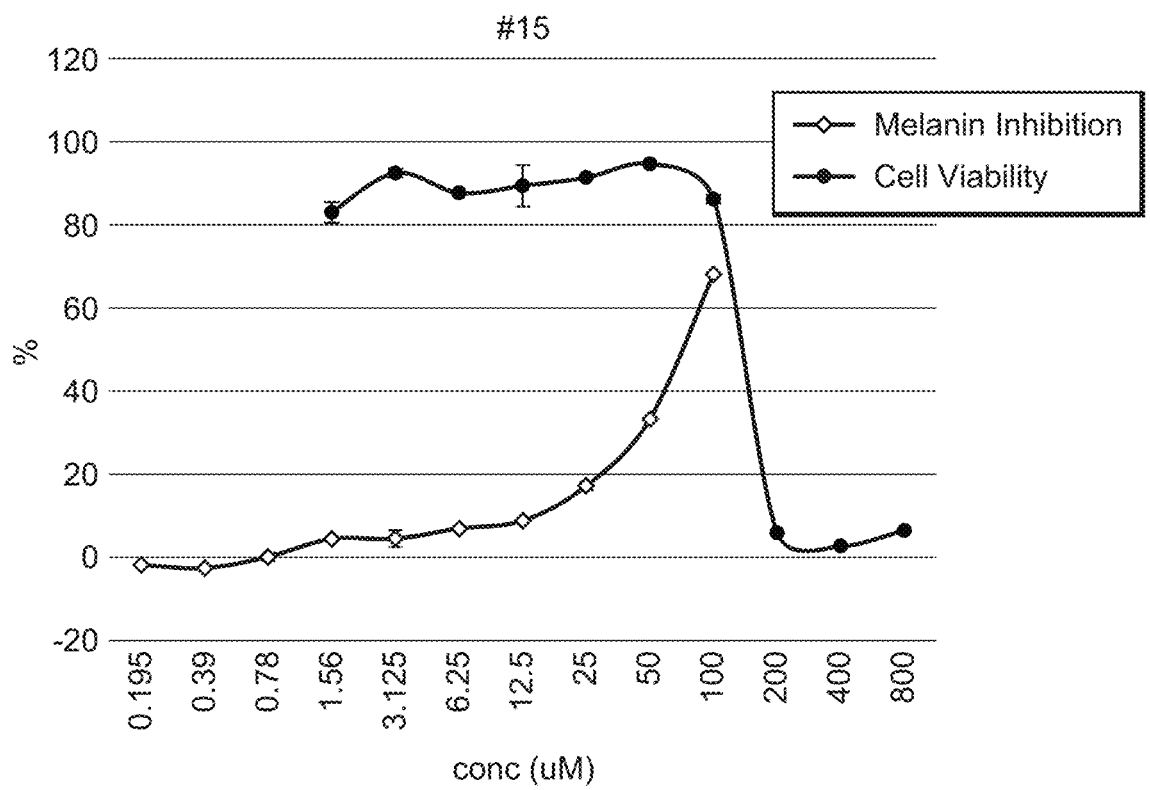
FIG. 8 illustrates graphically a profile of the inhibition in the production of melanin by (Z)-5-(4,8-Dimethylnona-1,7-dienyl) benzene-1,3-diol (15) as described in Example 5. The data is presented as melanin content (% of untreated control) vs. inhibitor concentration (μM). The $IC_{50}$ of compound 15 was determined to be 74 μM.

The present disclosure provides pharmaceutical agents that have strong anti-melanogenic activity. The anti-melanogenic properties of representative compounds were evaluated by means of mushroom tyrosinase assay, inhibition of melanin production by murine B16-F1 melanoma cell and melanin inhibition in a reconstructed human skin model. Specifically, these compounds show inhibition of melanin production by murine B16-F1 melanoma cells as well as melanin inhibition in the reconstructed human skin model, but they show poor inhibitory activity on mushroom tyrosinase enzyme. This finding suggests that the active ingredients affect the modulators in one of the melanogenic signaling pathways (Prior Art FIG. 1), which has the end result of reducing the melanin in the tissue. This anti-melanogenic activity may be due to inhibition of other enzymes in melanogenesis, increased degradation or reduced expression of melanogenic enzymes, inhibition of other components of the melanogenesis signaling pathways, inhibition of structural proteins involved in melanogenesis, or decreased melanosome transport. Contemplated embodiments treat melanin-producing cells with each compound and measure global gene expression changes to determine which pathways are affected to ascertain the mechanism of action.

In addition, the present subject matter also possesses superior antimicrobial activity against *Propionibacterium* (p-acne) as well as potent inhibition of proinflammatory cytokines including COX-1, COX-2 and 5-LOX.

The strong antimicrobial properties of a representative compound were evaluated by MIC/MBC test against *Propionibacterium* (p-acne). The anti-inflammation properties were evaluated by inhibitory assay against proinflammatory enzymes including COX-1, COX-2 and 5-LOX.

Compounds of formula I are described herein:

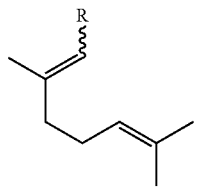

Formula I wherein R comprises an aromatic or heteroaromatic ring selected from the group consisting of phenyl, naphthyl, biphenyl, 2-pyridyl, 3-pyridyl, 4-pyridyl, 2-furanyl, 3-furanyl; wherein R is substituted with 1 to 3 moieties (R', R", R''') independently selected from the group consisting of a $C_1$-$C_{10}$ alkyl group, a $C_1$-$C_{10}$ alkoxy group or a hydroxyl group.

Compounds of formula II are described herein:

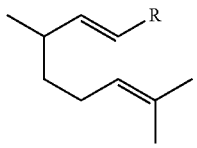

Formula II wherein R comprises an aromatic or heteroaromatic ring selected from the group consisting of phenyl, naphthyl, biphenyl, 2-pyridyl, 3-pyridyl, 4-pyridyl, 2-furanyl, 3-furanyl; wherein R is substituted with 1 to 3 moieties (R', R", R'") independently selected from the group consisting of a $C_1$-$C_{10}$ alkyl group, a $C_1$-$C_{10}$ alkoxy group or a hydroxyl group.

Compounds of formula III are described herein:

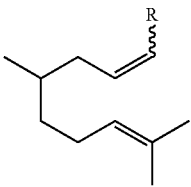

Formula III wherein R comprises an aromatic or heteroaromatic ring selected from the group consisting of phenyl, naphthyl, biphenyl, 2-pyridyl, 3-pyridyl, 4-pyridyl, 2-furanyl, 3-furanyl; wherein R is substituted with 1 to 3 moieties (R', R", R'") independently selected from the group consisting of a $C_1$-$C_{10}$ alkyl group, a $C_1$-$C_{10}$ alkoxy group or a hydroxyl group.

Compositions comprising (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy) acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy) diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy)diacetic acid (17) or a pharmaceutically acceptable salt thereof are disclosed herein alone or in combination with one another.

Methods for inhibiting the production of melanin are disclosed comprising administering to a subject in need thereof a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing and treating diseases and conditions related to the overproduction or uneven distribution of melanin comprising administering to a subject in need thereof an effective amount of a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy) diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for whitening and/or lightening skin comprising administering to a subject in need thereof a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing melanin synthesis wherein the symptom, condition, disorder, or disease associated tyrosinase inhibition comprising administering to a subject in need thereof an effective amount of a composition are disclosed herein comprising at least one of the following compounds:

(E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy) diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing melanin synthesis wherein the symptom, condition, disorder, or disease associated non-tyrosinase inhibition comprising administering to a subject in need thereof an effective amount of a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for preventing and treating diseases wherein the symptom, condition, disorder, or disease associated with free radicals, oxidative stress, UV rays induced skin damages, skin aging, skin inflammatory diseases or disorders, skin degenerative diseases or disorders comprising administering to a subject in need thereof an effective amount of a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl) phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy) acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy) diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy)diacetic acid (17) or a pharmaceutically acceptable salt thereof.

Methods for inhibit the browning and color changes in fruits, vegetables, juices and other food products comprising administering a compound are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy) diacetic acid (10); (E)-2,2'-(4-(3,7-dimethylocta-1,6-dienyl)-1,3-phenylene)bis(oxy)diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

Methods for suppressing the activity of *Propionibacterium* (p-acnes) comprising administering to a patient in need thereof a composition are disclosed herein comprising at least one the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6-dienyl)-1,3-phenylene)bis(oxy) diacetamide (11); (E)-3-(3,7-dimethylocta-1,6-dienyl) pyridine (12); (E)-2-(3,7-dimethylocta-1,6-dienyl) pyridine (13), (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy)diacetic acid (17) or a pharmaceutically acceptable salt thereof.

Methods for deactivating the activity of proinflammatory cytokines, such as COX-1, COX-2, and 5-LOX comprising administering to a patient in need thereof a composition are disclosed herein comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4); (E)-4-(3,7-dimethylocta-1,6-dienyl)phenol (5); (E)-4-(3,7-dimethylocta-1,6-dienyl) benzene-1,3-diol (6); (E)-5-(3,7-dimethylocta-1,6-dienyl) benzene-1,3-diol (7); E)-6-(3,7-dimethylocta-1,6-dienyl) naphthalene-2-ol (8); (E)-2-(4-(3,7-dimethylocta-1,6-dienyl)phenoxy)acetic acid (9); (E)-2,2'-(4-(3,7-dimethylocta-1,6-dienyl)-1,3-phenylene)bis(oxy)diacetic acid (10); (E)-2,2'-(4-(3,7-dimethylocta-1,6- dienyl)-1,3-phenylene)bis(oxy)diacetamide (11); (E)-3-(3, 7-dimethylocta-1,6-dienyl) pyridine (12); (E)-2-(3,7-dimethylocta-1,6-dienyl) pyridine (13); (E)-5-(3,7-dimethylocta-1,6-dienyl)-2-methoxypyridine (14); (Z)-5-(4,8-dimethylnona-1,7-dienyl) benzene-1,3-diol (15); (E)-5-(4,8-dimethylnona-1,7-dienyl) benzene-1,3-diol (16); (E)-2,2'-(5-(4,8-dimethylnona-1,7-dienyl)-1,3-phenylene)bis(oxy) diacetic acid (17) or a pharmaceutically acceptable salt thereof.

These before mentioned methods are contemplated to be effective with diseases and conditions that comprise, and in some instances consist of, suntan, hyper pigmentation spots caused by skin aging, melasma, liver diseases, thermal burns and topical wounds, skin pigmentation due to inflammatory conditions caused by fungal, microbial and viral infections, vitiligo, carcinoma, melanoma, as well as other mammalian skin conditions.

In some embodiments, these methods are contemplated effective with post inflammatory hyperpigmentation (PIH) that is derived from acne, atopic dermatitis, allergic contact dermatitis, incontinent pigmentation, lichen planus, lupus erythematosus, morphea, mechanical trauma, ionizing or nonionizing radiation, burns, laser or drug therapies, skin infection or combinations thereof.

The present subject matter also includes a novel composition of matter comprised of dienes, wherein said dienes are selected from the group of compounds represented by the following general structure:

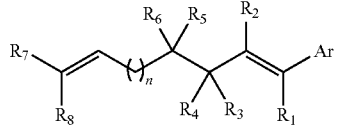

Wherein, "Ar" the term "aromatic" as used herein refers to any compound which includes or consists of one or more hydrocarbon aromatic rings. The rings may be mono or polycyclic ring systems. Examples of suitable rings include, but are not limited to benzene, naphthalene, biphenyl, terphenyl etc. Ar is independently selected from the group consisting of a substituted 5- or 6-membered aromatic or heteroaromatic ring, wherein each 6-membered aromatic or heteroaromatic ring is independently substituted with 1-5 R' groups consisting of —H, —OH, —SH, —OR, —CN, —SR, —NH$_2$, —NHR, —NR$_2$, X, Wherein, X is a halogen, selected from the group consisting of Cl, Br, F, I; R$_{1-8}$, are independently selected from the group consisting of —H, an alkyl, alkenyl group can be substituted or optionally unsubstituted with one or more substituents having between 1-20 carbon atoms, and n=0 to 5. In a preferred embodiment n=0-2.

In one contemplated embodiment, said dienes are selected from the group of compounds represented by the following general structure:

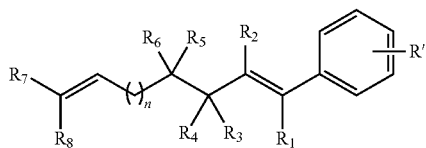

Wherein, R$_{1-8}$, are independently selected from the group consisting of —H, an alkyl, alkenyl group can be substituted or optionally unsubstituted with one or more substituents having between 1-20 carbon atoms, and n=0 to 5. In a preferred embodiment n=0-2.

In a contemplated embodiment, the present disclosure provides pharmaceuticals and cosmeceuticals agent that are depicted in Formula I-III. These compounds or their pharmaceutically acceptable salts, not limited to racemic version, but also apply to single enantiomer with preferred position. These compounds or their pharmaceutically acceptable salts also not only limited to preferred geometrical isomer, either E/or Z, but a mixture in composition.

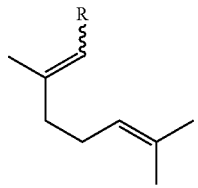

Formula I

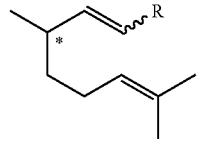

Formula II

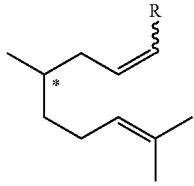

Formula III

These compounds or their pharmaceutically acceptable salts thereof are shown to be useful for both cosmeceuticals and pharmaceuticals applications.

These compounds also showed anti-melanogenic property with low cytotoxicity. The anti-melanogenic properties were evaluated by means of tyrosinase inhibitory activity as well as, the inhibition of melanin production by murine B16-F1 melanoma cells. Illustrated is the inhibitory activity of representative compounds against mushroom tyrosinase, as well as, the inhibition of melanin production by murine B16-F1 melanoma cells as described in Examples 4 and 5. The skin whitening properties of representative compounds were evaluated by means of a reconstructed human skin model as described in Example 6. These compounds or their pharmaceutically acceptable salts thereof are shown to be useful for both cosmetic and medical applications as detailed below.

These compounds are shown to have excellent antimicrobial property against *Propionibacterium* (p-acne bacterium), a gram-positive bacteria, in single digit ppm level. The antimicrobial properties of representative compounds were evaluated by means of inhibitory activity against *P-acnes* bacterium described in Example 7.

These compounds also showed excellent anti-inflammatory property against post-inflammatory cytokines such as COX-1, COX-2, and 5-LOX. The antimicrobial properties of representative compounds were evaluated by means of inhibitory activity against post-inflammatory cytokines such as COX-1, COX-2, and 5-LOX as described in Example 8.

As used in this context, the term "derivative" or "analog" refers to a compound having similar chemical structure or function as the compounds of Formula I-III that retains the core dienes, either 1,5-, 1,6-, or 1-7-dienes with substituted aromatic ring.

Various terms are used herein to refer to aspects of the present subject matter. To aid in the clarification of the description of the components of this subject matter, the following definitions are provided. Unless defined otherwise all technical and scientific terms used herein have the meaning commonly understood by one of ordinary skill in the art to which this subject matter belongs.

It is to be noted that as used herein the term "a" or "an" entity refers to one or more of that entity; for example, a tyrosinase inhibitor refers to one or more tyrosinase inhibitors. As such, the terms "a" or "an", "one or more" and "at least one" are used interchangeably herein.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "dienes" as used herein refers to a straight or branched chain, unsaturated hydrocarbon having the indicated number of carbon atoms. For example, (C1-C10) alkenyl is meant to include a straight or branched chain hydrocarbon having one to ten carbon atoms. An alkenyl group can be substituted or optionally unsubstituted with one or more substituents as described herein.

The term "aromatic" as used herein refers to any compound which includes or consists of one or more hydrocarbon aromatic rings. The rings may be mono or polycyclic ring systems. Examples of suitable rings include, but are not limited to benzene, naphthalene, biphenyl, triphenyl etc.

As used herein, the term "heteroatom" is meant to include oxygen (O), nitrogen (N) and sulfur (S). The term "heteroaromatic" as used herein refers to an aromatic heterocyclic ring of 5 to 14 members and having at least one heteroatom selected from nitrogen, oxygen and sulfur, and containing at least 1 carbon atom. Representative heteroaromatics include pyridyl, furyl, thienyl, pyrrolyl and imidazoly] etc. The heteroary! group can be attached via any heteroatom or carbon atom, where chemically acceptable. A heteroaryl group can be unsubstituted or optionally substituted with one or more substituents as described herein.

As used herein, the term "heterocycle" refers to non-aromatic 5 to 14-membered ring systems which are either saturated, unsaturated and which contain from 1 to 4 heteroatoms independently selected from nitrogen, oxygen and sulfur, and wherein the nitrogen and sulfur heteroatoms can be optionally oxidized, and the nitrogen heteroatom can be optionally quaternized. The heterocycle can be attached via any heteroatom or carbon atom, where chemically acceptable. Representative examples of non-aromatic heterocycles include, but are not limited to tetrahydrofuranyl, tetrahydropyrrolyl, pyranyl and tetrahydropyrany] etc. A heterocycle group can be unsubstituted or optionally substituted with one or more substituents as described herein.

"Therapeutic" as used herein, includes prevention, treatment and/or prophylaxis. When used therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of biological system that is desired. The precise dosage will vary according to a variety of factors, including but not limited to the age and size of the subject, the disease and the treatment being effected.

A "host" or "patient" or "subject" is a living mammal, human or animal, for whom therapy is desired. The "host," "patient" or "subject" generally refers to the recipient of the therapy to be practiced according to the method of the subject matter. It should be noted that the subject matter described herein may be used for veterinary as well as human applications and that the term "host" should not be construed in a limiting manner. In the case of veterinary applications, the dosage ranges can be determined as described below, taking into account the body weight of the animal.

As used herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to, such sterile liquids as water and oils.

A "pharmaceutically acceptable salt" or "salt" of a tyrosinase inhibitor is a product of the disclosed compound that contains an ionic bond and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulpho-nates, arylsulpho-nates, arylalkylsulfonates. acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the subject matter is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. Examples of substituents include, but are not limited to $C_1$-$C_{10}$ alkyl, hydroxy (—OH), $C_1$-$C_{10}$ alkoxy groups. Typically, an aromatic, heteroaromatic or heterocyclic ring will have from 1-3 substituents.

In a contemplated embodiment, the present subject matter provides a compound having a structure shown in Formula I, or a pharmaceutically acceptable salt thereof:

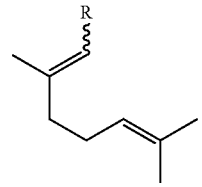

Formula I

Wherein R is selected from a substituted or unsubstituted aromatic, heteroaromatic or heterocyclic ring. In one embodiment R comprises, and in some instances is selected from the group consisting of, a substituted or unsubstituted: phenyl, biphenyl, 2-pyridyl, 3-pyridyl, 4-pyridyl, 2-furanyl, 3-furanyl. In one embodiment R is substituted with 1 to 3 moieties (R', R", R™) comprises, and in some instances is selected from the group consisting of, a $C_1$-$C_{10}$ alkyl group, a $C_1$-$C_{10}$ alkoxy group or a hydroxyl group. In other embodiments R is selected from the group consisting of 1'-(4'-methoxy)pheny]; 1'-(2,4-dihydroxy)phenyl; 1'-(3-pyridyl); 1'-(bi-phenyl-4-ol).

In one of its aspects the present subject matter provides a compound having a structure shown in Formula II or a pharmaceutically acceptable salt thereof.

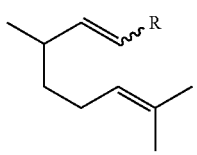

Formula II

Wherein R comprises, and in some instances is selected from the group consisting of, a substituted or unsubstituted: phenyl, biphenyl, 2-pyridyl, 3-pyridyl, 4-pyridyl, 2-furanyl, 3-furanyl. In one embodiment R is substituted with 1 to 3 moieties (R', R", R™) independently comprising, and in some instances is selected from the group consisting of, a $C_1$-$C_{10}$ alkyl group, a $C_1$-$C_{10}$ alkoxy group or a hydroxyl group. In other embodiments R comprises, and in some instances is selected from the group consisting of, 1'-(4'-methoxy)pheny]; 1'-(2,4-dihydroxy)phenyl; 1'-(3-pyridyl); 1'-(bi-phenyl-4-ol).

In one contemplated embodiment, the present subject matter provides a compound having a structure shown in Formula III or a pharmaceutically acceptable salt thereof.

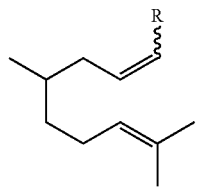

Formula III

Wherein R is selected from a substituted or unsubstituted aromatic, heteroaromatic or heterocyclic ring. In one embodiment R comprises, and in some instances is selected from the group consisting of, a substituted or unsubstituted: phenyl, biphenyl, 2-pyridyl, 3-pyridyl, 4-pyridyl, 2-furanyl, 3-furanyl. In one embodiment R is substituted with 1 to 3 moieties (R', R", R™) independently comprising, and in some instances is selected from the group consisting of, a $C_1$-$C_{10}$ alkyl group, a $C_1$-$C_{10}$ alkoxy group or a hydroxyl group. In other embodiments R is selected from the group consisting of 1'-(4'-methoxy)pheny]; 1'-(2,4-dihydroxy)phenyl; 1'-(3-pyridyl); 1'-(bi-phenyl-4-ol).

Table 1 lists representative novel 1,5-dienes analogs of Formula I which are useful for anti-melanogenic. The synthetic methods that can be used to prepare each compound, identified in Table 1 are described in detail in Example 1. Supporting 1H- and 13C-NMR data is provided for each compound synthesized. In general, the compounds of Formula I can be synthesized from readily available materials using standard organic synthesis techniques. Further preparation routes may be found in the literature and relevant art.

TABLE 1

Compounds Representative of Formula: Anti-melanogenic property

| Compound | Structure | Anti-melanogenic | | |
|---|---|---|---|---|
| | | MUSHROOM TYROSINASE | MELANIN PRODUCTION | CELL VIABILITY |
| (E)-4-(2,6-Dimethylhepta-1,5-dienyl)phenol (1) | 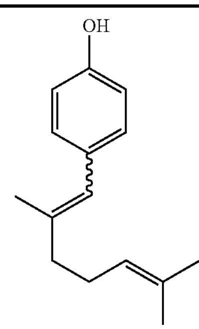 | Not active | 158 μm | 269 μm |
| (E)-3-(2,6-Dimethylhepta-1,5-dienyl)phenol (2) | 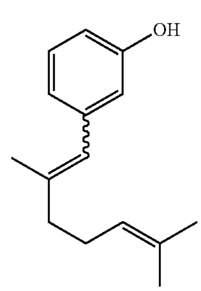 [SMILES: CC(C)=CCCC(C)=Cc1cccc(O)c1] | Not active | 82 μm | 66 μm |

TABLE 1-continued

Compounds Representative of Formula: Anti-melanogenic property

| Compound | Structure | MUSHROOM TYROSINASE | MELANIN PRODUCTION | CELL VIABILITY |
|---|---|---|---|---|
| (E)-4-(2,6-Dimethylhepta-1,5-dienyl)benzene-1,3-diol (3) | 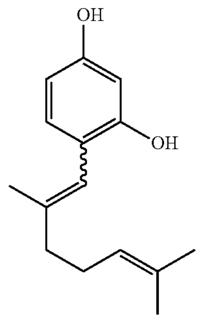 [SMILES: CC(C)=CCCC(C)=Cc1ccc(O)cc1O] | Not active | 164 μm | 172 μm |
| (E)-5-(2,6-Dimethylhepta-1,5-dienyl)benzene-1,3-diol (4) | 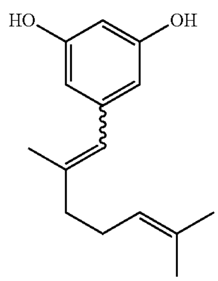 [SMILES: CC(C)=CCCC(C)=Cc1cc(O)cc(O)c1] | Not active | 72 μm | 127 μm |

Table 2 lists representative novel 1,6-dienes analogs of Formula II which are useful as anti-melanogenic. The synthetic methods that can be used to prepare each compound, identified in Table 1 are described in detail in Example 2. Supporting 1H- and 13C-NMR data is provided for each compound synthesized. In general, the compounds of Formula I can be synthesized from readily available materials using standard organic synthesis techniques. Further preparation routes may be found in the literature and relevant art.

TABLE 2

Compounds Representative of Formula II: Anti-melanogenic property

| Compound | Structure | MUSHROOM TYROSINASE | MELANIN PRODUCTION | CELL VIABILITY |
|---|---|---|---|---|
| (E)-4-(3,7-Dimethylocta-1,6-dienyl)phenol (5) | 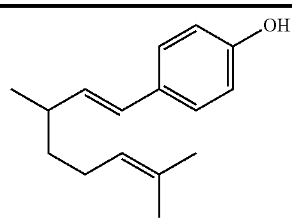 | N/A | 72 μm | 50 μm |
| (E)-4-(3,7-Dimethylocta-1,6-dienyl) benzene-1,3-diol (6) | 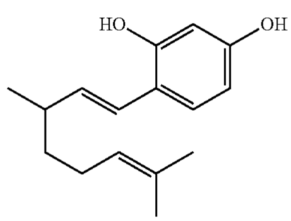 [SMILES: CC(C)=CCCC(C)/C=C/c1ccc(O)cc1O] | 20 μm | 9 μm | 233 μm |

TABLE 2-continued

Compounds Representative of Formula II: Anti-melanogenic property

| Compound | Structure | Anti-melanogenic | | |
|---|---|---|---|---|
| | | MUSHROOM TYROSINASE | MELANIN PRODUCTION | CELL VIABILITY |
| (E)-5-(3,7-Dimethylocta-1,6-dienyl) benzene-1,3-diol (7) | | 492 μm (theoretical) | 97 μm | 152 μm |
| E)-6-(3,7-Dimethylocta-1,6-dienyl) naphthalene-2-ol (8) | | Not active | 22 μm | 68 μm |
| (E)-2-(4-(3,7-Dimethylocta-1,6-dienyl)phenoxy)acetic acid (9) | | NA | NA | NA |
| (E)-2,2'-(4-(3,7-Dimethylocta-1,6-dienyl)-1,3-phenylene)bis(oxy)diacetic acid (10) | | NA | NA | NA |
| (E)-2,2'-(4-(3,7-Dimethylocta-1,6-dienyl)-1,3-phenylene)bis(oxy)diacetamide (11) | | NA | NA | NA |

TABLE 2-continued

Compounds Representative of Formula II: Anti-melanogenic property

| Compound | Structure | Anti-melanogenic | | |
|---|---|---|---|---|
| | | MUSHROOM TYROSINASE | MELANIN PRODUCTION | CELL VIABILITY |
| (E)-3-(3,7-Dimethylocta-1,6-dienyl) pyridine (12) | | Not active | 74 μm | 385 μm |
| (E)-2-(3,7-Dimethylocta-1,6-dienyl) pyridine (13) | | Not active | 149 μm | 650 μm |
| (E)-5-(3,7-Dimethylocta-1,6-dienyl)-2-methoxypyridine (14) | | Not active | 147 μm | 369 μm |

Table 3 lists representative novel 1,6-dienes analogs of Formula II which are useful as anti-melanogenic. The synthetic methods that can be used to prepare each compound, identified in Table 3 are described in detail in Example 3. Supporting 1H- and 13C-NMR data is provided for each compound synthesized. In general, the compounds of Formula I can be synthesized from readily available materials using standard organic synthesis techniques. Further preparation routes may be found in the literature and relevant art.

TABLE 3

Compounds Representative of Formula III: Anti-melanogenic property

| Compound | Structure | Anti-melanogenic | | |
|---|---|---|---|---|
| | | MUSHROOM TYROSINASE | MELANIN PRODUCTION | CELL VIABILITY |
| (Z)-5-(4,8-Dimethylnona-1,7-dienyl) benzene-1,3-diol (15) | | Not active | 158 μm | 269 μm |
| (E)-5-(4,8-Dimethylnona-1,7-dienyl) benzene-1,3-diol (16) | | Not active | 164 μm | 172 μm |

TABLE 3-continued

Compounds Representative of Formula III: Anti-melanogenic property

| Compound | Structure | Anti-melanogenic | | |
|---|---|---|---|---|
| | | MUSHROOM TYROSINASE | MELANIN PRODUCTION | CELL VIABILITY |
| (E)-2,2'-(5-(4,8-Dimethylnona-1,7-dienyl)-1,3-phenylene)bis(oxy)diacetic acid (17) | | Not active | 72 μm | 127 μm |

The antimicrobial activity was determined of the selected compounds against a Gram-positive—*Propionibacterium* (p-acnes). The MIC and MBC values showed (Table 4) that the remarkable inhibition of the bacterial growth was shown against the tested organisms.

The anti-inflammatory activity was determined of the selected compounds against a by the COX-1, COX-2, and 5-LOX assays as described in Example 5 are also set forth in Table 4. For select compounds of Formula I-III, Table 4 provides $IC_{50}$ values as determined by the COX-1, COX-2, and 5-LOX assays described in Example 5.

TABLE 4

Compounds Representative of Formula I-III: Anti-acne property

| Compound | Structure | Anti-microbial (p-acne) | | Anti-inflammatory ($IC_{50}$) | | |
|---|---|---|---|---|---|---|
| | | MIC | MBC | COX-1 | COX-2 | 5-LOX |
| (E/Z)-4-(2,6-Dimethylhepta-1,5-dienyl)phenol (1) | | <3.9 ppm | <3.9 ppm | 122 μm | Not active | 90 μm |

TABLE 4-continued

Compounds Representative of Formula I-III: Anti-acne property

| Compound | Structure | Anti-microbial (p-acne) | | Anti-inflammatory (IC$_{50}$) | | |
| --- | --- | --- | --- | --- | --- | --- |
| | | MIC | MBC | COX-1 | COX-2 | 5-LOX |
| (E/Z)-4-(2,6-Dimethylhepta-1,5-dienyl)benzene-1,3-diol (3) | | <3.9 ppm | <3.9 ppm | — | — | — |
| (E/Z)-5-(2,6-Dimethylhepta-1,5-dienyl)benzene-1,3-diol (4) | | <3.9 ppm | <3.9 ppm | 64 μm | 245 μm | 317 μm |
| (E)-4-(3,7-Dimethylocta-1,6-dienyl)phenol (5) | | 7.8 ppm | 15.6 ppm | No Inhibition | 72 μm | 50 μm |
| (E)-4-(3,7-Dimethylocta-1,6-dienyl) benzene-1,3-diol (6) | | 3.9 ppm | 3.9-31.3 ppm | 74 μm | 164 μm | 307 μm |
| (E)-5-(3,7-Dimethylocta-1,6-dienyl) benzene-1,3-diol (7) | | 7.8 ppm | 7.8-31.3 ppm | 25 μm | 135 μm | 143 μm |
| E)-6-(3,7-Dimethylocta-1,6-dienyl) naphthalene-2-ol (8) | | <3.9 ppm | <3.9 ppm | | | |

TABLE 4-continued

Compounds Representative of Formula I-III: Anti-acne property

| Compound | Structure | Anti-microbial (p-acne) | | Anti-inflammatory (IC$_{50}$) | | |
|---|---|---|---|---|---|---|
| | | MIC | MBC | COX-1 | COX-2 | 5-LOX |
| (E)-3-(3,7-Dimethylocta-1,6-dienyl) pyridine (12) | | <3.9 ppm | <3.9 ppm | | | |
| (Z)-5-(4,8-Dimethylnona-1,7-dienyl) benzene-1,3-diol (15) | | <3.9 ppm | <3.9 ppm | 122 μm | No Inhibition | 90 μm |
| (E)-5-(4,8-Dimethylnona-1,7-dienyl) benzene-1,3-diol (16) | | <3.9 ppm | <3.9 ppm | | | |
| (E)-2,2'-(5-(4,8-Dimethylnona-1,7-dienyl)-1,3-phenylene)bis (oxy)diacetic acid (17) | | <3.9 ppm | <3.9 ppm | | | |

MIC: the lowest level of antimicrobial agent that inhibits growth.
MBC: the lowest concentration of an antimicrobial agent required to kill a particular Bacterium.

Table 5 lists representative novel 1,6-dienes analogs of Formula I-III which are useful as anti-oxidant. ORAC 5.0 consists of five types of ORAC assays that evaluate the antioxidant capacity of material against five primary reactive oxygen species (ROSs, commonly called "oxygen radicals") found in humans: peroxyl radical, hydroxyl radical, superoxide anion, singlet oxygen, and peroxynitrile. Trolox is used as reference standard, and the results are expressed as μ mole Trolex equivalency per gram (or milliliter) of a tested material.

Compounds Representative of Formula I-III: Antioxidant property

| Compound | Structure | ORAC (μ mole TE/gram) |
| --- | --- | --- |
| (E)-5-(2,6-Dimethylhepta-1,5-dienyl)benzene-1,3-diol (4) | 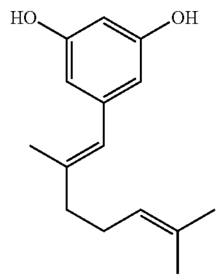 | 22580 |
| (E)-4-(3,7-Dimethylocta-1,6-dienyl)phenol (5) | 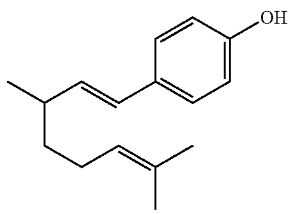 [SMILES: CC(C)=CCCC(C)/C=C/c1ccc(O)cc1] | 37643 |
| (E)-4-(3,7-Dimethylocta-1,6-dienyl) benzene-1,3-diol (6) | 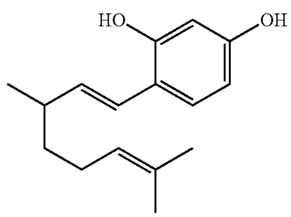 [SMILES: CC(C)=CCCC(C)/C=C/c1ccc(O)cc1O] | 45869 |
| (E)-5-(3,7-Dimethylocta-1,6-dienyl) benzene-1,3-diol (7) | 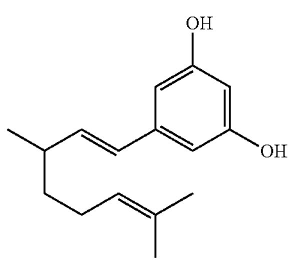 [SMILES: CC(C)=CCCC(C)/C=C/c1cc(O)cc(O)c1] | 18196 |
| (Z)-5-(4,8-Dimethylnona-1,7-dienyl) benzene-1,3-diol (15) | 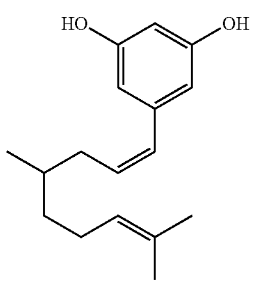 [SMILES: CC(C)=CCCC(C)C/C=C\c1cc(O)cc(O)c1] | 11951 |

EXAMPLES

Example 1: General and Specific Methods for the Synthesis of Compounds of Formula I Compounds of Formula I were prepared generally as set forth in Scheme 1, using a substituted benzylphosphonate as R for purposes of illustration. The phosphonate reagents were prepared from the corresponding benzyl bromide treated with triethyl phosphite following Arbuzov Reaction. Briefly, the 1,5-dienes compounds of Formula I were prepared by Wittig reaction from the corresponding phosphonate salt with appropriate ketone. Then the coupled diene product was treated with methyl magnesium iodide for demethylation reaction to get the desired phenol dienes.

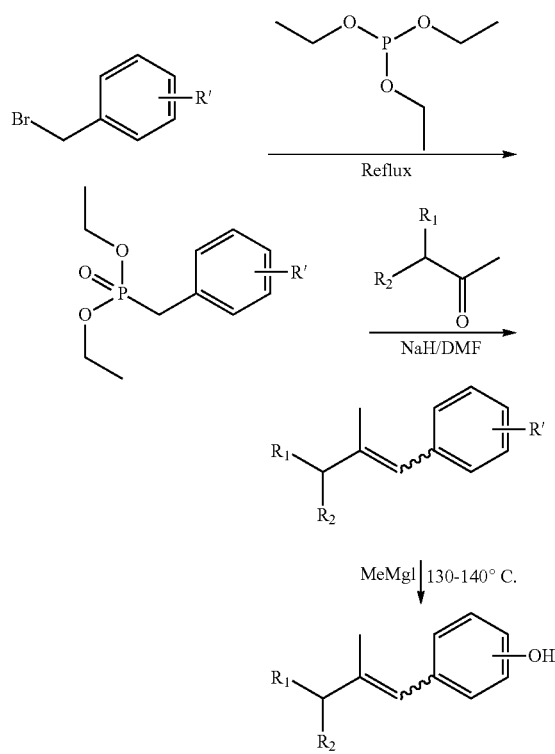

Representative Procedure for Scheme 1:
Synthesis of (E/Z)-4-(2,6-Dimethylhepta-1,5-dienyl)phenol (1):

General/Typical Procedure for synthesis of phosphonate salt by Arbuzov Reaction: A solution of 4-methoxybenzylbromide (20 g, 100 mmol) in P(OEt)$_3$ (23 mL, 140 mmol) was refluxed for 5 h followed by removal of bromoethane and excess triethyl phosphite by distillation at reduced pressure. The residue provided 24.5 g (95%) of product which was enough pure for next step.

General/Typical Procedure for Wittig reaction: To a solution of the phosphonium salt of benzyl bromide (12 g, 46 mmol) and 6-methyl-5-hepten-2-one (5.3 g, 42 mmol) in anhydrous DMF (50 mL), NaH (60% dispersion in mineral oil, 46 mmol) was added at 0° C. portion wise. The reaction mixture was allowed to stir 0° C. for 1 h, during which time the mixture developed a red color indicating the formation of ylide. After stirring at room temperature for 3 h, the reaction is complete. The mixture is diluted with water at 0° C. and the product is extracted with EtOAc. The organic layer is washed with saturated aqueous NaHCO$_3$ and brine then dried over Na$_2$SO$_4$. The solvent is removed under reduced pressure and the yellow residue was passed through a short bed of silica gel eluting with ethyl acetate-hexane (5:95) to yield the coupled product (9.7 g, 92%) in a ratio of (E/Z: 80:20) as a pale yellow oil.

General/Typical Procedure for demethylation reaction: To a solution (7 g, 21.8 mmol) in 10 ml of Et$_2$O was added a solution of MeMgI (3M) in Et$_2$O (10.0 ml, 30 mmol). The solvent was removed under reduced pressure, and the residue was heated under argon at 130-140° C. for 10 min. The mixture was cooled to rt, and the reaction was quenched with 10 ml of saturated aqueous NH$_4$CL solution. The product was extracted with EtOAc (3×100 ml). The combined organic phase was washed with brine and dried over Na$_2$SO$_4$. The solvent was removed under reduced pressure, and the crude product was purified by column chromatography (silica gel; AcOEt/hexane 1:10) to afford the title compound (2.6 g, 55%).

(E/Z)-4-(2,6-Dimethylhepta-1,5-dienyl)phenol (1): $^1$H-NMR (CDCl$_3$, 500 MHz): Major (E): 7.12 (d, 2H, J=10 Hz), 6.79 (d, 2H, J=10 Hz), 6.20 (s, IH), 5.18-5.15 (m, IH), 2.25-2.14 (m, 4H), 1.84 (s, 3H), 1.71 (s, 3H), 1.64 (s, 3H); Minor (Z): 7.08 (d, 2H, J=10 Hz), 6.77 (d, 2H, J=10 Hz), 6.21 (s, IH), 5.13-5.10 (m, IH), 2.25-2.14 (m, 4H), 1.87 (s, 3H), 1.68 (s, 3H), 1.61 (s, 3H). $^{13}$C-NMR (CDCl3, 125 MHz): 153.66 (C), 138.71 (C), 131.92 (C), 131.61 (C), 130.21 (CH), 129.96 (2CH), 124.21 (CH), 115.08 (2 CH), 40.89 (CH$_2$), 26.95 (CH$_2$), 25.83 (CH$_3$) 17.92 (CH$_3$), 17.81 (CH$_3$).

Representative compounds 2-4 of Formula I (Table 1) were synthesized according to the same general reaction scheme using the appropriate staring materials. Overall yields varied from 30-48%.

(E/Z)-4-(2,6-Dimethylhepta-1,5-dienyl)benzene-1,3-diol (2): $^1$H-NMR (CDCl$_3$, 500 MHz): 7.16 (d, IH, J=7.5 Hz), 6.78 (d, 2H, J=8 Hz), 6.70 (s, IH), 6.66-6.64 (m, IH), 6.19 (s, 1H), 5.16-5.12 (m, 1H), 2.16-2.11 (m, 4H), 1.84 (s, 3H), 1.68 (s, 3H), 1.62 (s, 3H); Minor (Z): 7.13 (d, IH, J=7.5 Hz), 6.76 (d, 1H, J=8 Hz), 6.63 (s, 1H), 6.18 (s, IH), 5.10-5.08 (m, IH), 2.25-2.121 (m, 4H), 1.86 (s, 3H), 1.66 (s, 3H), 1.61 (s, 3H). $^{13}$C-NMR (CDCl$_3$, 125 MHz): 155.22 (C), 140.41 (C), 139.43 (C), 131.90 (CH), 129.25 (CH), 125.39 (C), 124.63 (CH), 121.57 (CH), 115.05 (CH), 113.05 (CH), 40.82 (CH$_2$), 26.77 (CH$_2$), 25.74 (CH$_3$), 24.12 (CH$_3$), 17.95 (CH$_3$).

(E/Z)-5-(2,6-Dimethylhepta-1,5-dienyl)benzene-1,3-diol (3): $^1$H-NMR (CDCl$_3$, 500 MHz): 7.83 (d, IH, J=8 Hz), 6.38 (s, 1H), 6.19 (d, 1H, J=7.5 Hz), 6.14 (dd, IH, J=2.5 Hz), 5.16-5.14 (m, 1H), 2.19-2.16 (m, 4H), 1.87 (s, 3H), 1.65 (s, 3H), 1.60 (s, 3H); Minor (Z): 6.25 (d, 2H, J=2.5 Hz), 6.11 (s, 1H), 5.46 (s, IH), 5.10-5.08 (m, IH), 2.23-2.21 (m, 4H), 1.83 (s, 3H), 1.65 (s, 3H), 1.58 (s, 3H). $^{13}$C-NMR (CDCl$_3$, 125 MHz): 156.65 (2C), 141.50 (C), 140.17 (C), 132.03 (C), 125.03 (C), 124.21 (CH), 124.08 (CH), 108.69 (CH), 100.65 (CH), 40.82 (CH$_2$), 26.88 (CH$_2$), 26.80 (CH$_3$), 18.23 (CH$_3$), 17.93 (CH$_3$).

(E/Z)-4-(3,7-Dimethylocta-1,6-dienyl)phenol (4): $^1$H-NMR (CDCl$_3$, 500 MHz): 6.28 (d, IH, J=2.5 Hz), 6.19 (dd, 1H, J=2.5 & 2.5 Hz), 6.10 (s, IH), 5.47 (s, IH), 5.13-5.11 (m, 1H), 2.16-2.11 (m, 4H), 1.82 (s, 3H), 1.67 (s, 3H), 1.61 (s, 3H); Minor (Z): 6.25 (d, 2H, J=2.5 Hz), 6.11 (s, 1H), 5.46 (s, IH), 5.10-5.08 (m, IH), 2.23-2.21 (m, 4H), 1.83 (s, 3H), 1.65 (s, 3H), 1.58 (s, 3H). $^{13}$C-NMR (CDCl$_3$, 125 MHz): 159.57 (C), 157.56 (C), 142.47 (C), 141.27 (CH), 136.03 (C), 128.31 (C), 126.12 (CH), 122.08 (CH), 108.69 (CH), 103.57 (CH), 41.28 (CH$_2$), 27.68 (CH$_2$), 25.80 (CH$_3$), 18.63 (CH$_3$), 17.69 (CH$_3$).

Example 2: General and Specific Methods for the Synthesis of Compounds of Formula II Compounds of Formula II were prepared generally as set forth in Scheme 2, using a substituted bromobenzene as R for purposes of illustration. Briefly, the 1,6-dienes compounds of Formula II were prepared by Grignard addition reaction from the corresponding Grignard reagents with appropriate aldehyde. The Grignard reagents which was prepared with activated Mg turnings from the corresponding aryl bromide. Then the coupled product was treated with $POCl_3$ for dehydration reaction followed by demethylation reaction with MeMgI to get the desired phenol dienes.

Scheme 2

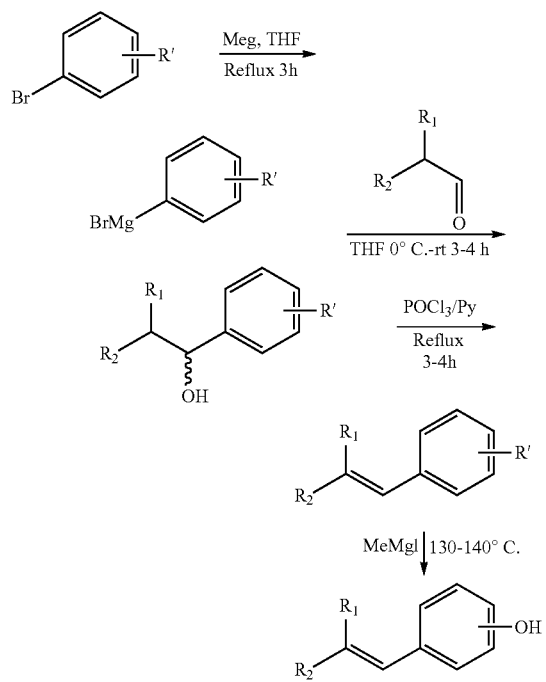

Representative Procedure for Scheme 2: Synthesis of (E)-4-(3,7-dimethylocta-1,6-dienyl)phenol (5):

General/Typical Procedure for Grignard addition reaction: 4-Bromoanisole (11.2 g. 60 mmol) in THF (60 ml) was added dropwise to magnesium turnings (1.9 g, 80 mmol) and iodine (a pinch) in THF (10 mL) in refluxing condition in argon media. After completing the addition, the reaction mixture was continued to reflux for another hour. Then the Grignard reagent was allowed to cool down to room temperature. The Grignard reagent was then added to a stirred solution of 2,6-Dimethyl-5-heptenal (6.4 g, 45 mmol) in THF (50 mL) at 0° C. in argon media and allowed to reach room temperature and continue stirring additional 3 h. After stirring at room temperature for 3 h, the reaction is complete. The reaction mixture was then cooled down at 0° C. and quenched with ammonium chloride, extracted with ethyl acetate, washed with brine and dried over anhydrous $Na_2SO_4$, filtered and concentrated in rotary evaporator and purified by column chromatography to yield (9.5 g, 80%) of the coupled product as liquid in 85:15 diastereomeric isomer.

General/Typical Procedure for dehydration reaction: The resulting coupled product (8.0 g, 31 mmol) was then treated with $POCl_3$ (7.4 g, 48 mmol) in pyridine (60 mL) solution and heated to reflux for 3 h. The reaction mixture was then cooled down and quenched with water, extracted with ethyl acetate, washed with brine and dried over anhydrous $Na_2SO_4$, filtered and concentrated in rotary evaporator and purified by column chromatography to yield (5.7 g, 75%) of the coupled product as a clear liquid as a single isomer.

General/Typical Procedure for demethylation reaction: The resulting alkoxy diene (5.4 g, 22 mmol) was dissolved in anhydrous diethyl ether (10 mL) and MeMgI (3M, 8.8 mL, 26.4 mmol) was added to the solution. The solvent was removed under reduced pressure, and the residue was heated under argon at 130-140° C. for 10 min. The mixture was cooled to rt, and the reaction was quenched with 10 ml of saturated aqueous $NH_4Cl$ solution, extracted with ethyl acetate, washed with brine and dried over anhydrous $Na_2SO_4$, filtered and concentrated in rotary evaporator and purified by column chromatography to get the title compound (5), yield (2.53 g, 50%).

Representative compounds 5-8 were synthesized according to the same protocol using appropriate staring materials. Overall yields varied from 40-50%.

$^1$H-NMR ($CDCl_3$, 500 MHz): 7.24 (d, 2H, J=8.5 Hz), 6.77 (d, 2H, J=8.5 Hz), 6.27 (d, IH, J=16 Hz), 5.95 (dd, IH, J=16, 8 Hz), 5.14-5.11 (m, 1H) 2.31-2.25 (m, 1H), 2.03-1.98 (m, 2H), 1.69 (s, 3H), 1.60 (s, 3H), 1.43-1.38 (m, 2H), 1.08 (d, 3H, J=6.5 Hz). $^{13}$C-NMR ($CDCl_3$, 125 MHz): 154.81 (C), 134.73 (CH), 131.48 (C), 130.96 (C), 128.53 (CH), 127.65 (CH), 127.86 (CH), 115.65 (CH), 115.60 (CH), 37.42 (CH), 36.94 ($CH_2$), 26.07 ($CH_2$), 25.91 ($CH_3$), 20.92 ($CH_3$), 17.91 ($CH_3$).

(E)-4-(3,7-Dimethylocta-1,6-dienyl) benzene-1,3-diol (6)
$^1$H-NMR (MeOD, 500 MHz): 7.15 (d, IH, J=10 Hz), 6.51 (d, IH, J=19 Hz), 6.26 (s, IH), 6.24 (d, IH, J=10 Hz), 5.89 (dd, IH, J=19, 10 Hz), 5.14-5.11 (m, 1H) 2.24-2.21 (m, 1H), 2.03-1.99 (m, 2H), 1.66 (s, 3H), 1.59 (s, 3H), 1.40-1.35 (m, 2H), 1.05 (d, 3H, J=5 Hz).
$^{13}$C-NMR (MeOD, 125 MHz): 158.28 (C), 156.34 (C), 134.16 (CH), 131.98 (C), 128.03 (CH), 125.90 (CH), 124.36 (CH), 118.41 (CH), 108.00 (CH), 38.69 (CH), 38.53 ($CH_2$), 27.00 ($CH_2$), 25.83 ($CH_2$), 21.52 ($CH_3$), 17.92 ($CH_3$).

(E)-5-(3,7-Dimethylocta-1,6-dienyl) benzene-1,3-diol (7)
$^1$H-NMR ($CDCl_3$, 500 MHz): 6.66 (d, IH, J=16 Hz), 6.53 (S, 1H), 6.34 (s, IH), 6.24 (S, IH), 6.06 (dd, IH, J=16, 8 Hz), 5.18-5.11 (m, 1H), 2.38-2.26 (M, 1H), 2.15-196 (m, 2H), 1.68 (s, 3H), 1.61 (s, 3H), 1.40-1.35 (m, 2H), 1.15 (d, 3H, J=7 Hz)

(E)-6-(3,7-Dimethylocta-1,6-dienyl) naphthalene-2-ol (8)
$^1$H-NMR ($CDCl_3$, 500 MHz): 7.67 (d, 2H, J=9 Hz), 7.60 (s, 1H), 7.58 (s, 1H), 7.53 (d, 1H, J=9 Hz), 7.70 (d, IH, J=9 Hz), 7.45 (d, IH, J=9 Hz), 6.45 (d, IH, J=16 Hz), 6.15 (dd, IH, J=16, 8 Hz), 5.15-5.12 (m, 1H), 2.36-2.32 (m, 1H), 2.06-2.0 (m, 2H), 1.69 (s, 3H), 1.60 (s, 3H), 1.46-1.43 (m, 2H), 1.11 (d, 3H, J=6.5 Hz). $^{13}$C-NMR ($CDCl_3$, 125 MHz): 153.30 (C), 136.48 (CH), 133.87 (C), 133.58 (C), 131.54 (C), 129.58 (CH), 128.37 (CH), 126.65 (CH), 125.39 (CH), 118.41 (CH), 109.63 (CH), 37.38 ($CH_3$), 37.09 ($CH_3$), 26.07 ($CH_2$), 25.89 ($CH_2$), 20.87 ($CH_3$), 17.90 (CH).

The acid derivative, 9 and 10 were synthesized by O-alkylation reaction with ethyl bromoacetate followed by base catalyzed hydrolysis from the corresponding phenolic dienes 5 and 6.

The acetamide derivative (11) was synthesized from 6 by O-alkylation reaction with 2-bromoacetamide.

(E)-2-(4-(3,7-Dimethylocta-1,6-dienyl)phenoxy)acetic acid (9)

$^1$H-NMR (MeOD, 500 MHz): 7.44 (d, 2H, J=8.5 Hz), 6.89 (d, 2H, J=8.5 Hz), 6.34 (d, IH, J=16 Hz), 6.15 (dd, IH, J=16, 8 Hz), 5.14-5.11 (m, 1H), 4.66 (s, 2H) 2.33-2.28 (m, 1H), 2.13-2.08 (m, 2H), 1.67 (s, 3H), 1.58 (s, 3H), 1.45-1.38 (m, 2H), 1.11 (d, 3H, J=6.5 Hz)

(E)-2,2'-(4-(3,7-Dimethylocta-1,6-dienyl)-1,3-phenylene)bis(oxy)diacetic acid (10):

$^1$H-NMR (MeOD, 500 MHz): 7.52 (d, IH, J=10 Hz), 6.66 (d, IH, J=19 Hz), 6.36 (s, IH), 6.28 (d, IH, J=10 Hz), 6.01 (dd, IH, J=19, 10 Hz), 5.18-5.14 (m, 1H), 4.63 (s, 2H), 4.58 (s, 2H), 2.34-2.21 (m, 1H), 2.13-2.08 (m, 2H), 1.76 (s, 3H), 1.69 (s, 3H), 1.40-1.35 (m, 2H), 1.15 (d, 3H, J=7 Hz).

(E)-2,2'-(4-(3,7-Dimethylocta-1,6-dienyl)-1,3-phenylene)bis(oxy)diacetamide (11): $^1$H-NMR (MeOD, 500 MHz): 7.98 (d, IH, J=8 Hz), 6.76 (d, IH, J=16 Hz), 6.46 (s, IH), 6.38 (d, IH, J=10 Hz), 6.01 (dd, IH, J=16, 10 Hz), 5.15-5.11 (m, 1H), 4.68 (s, 2H), 4.48 (s, 2H), 2.37-2.23 (m, 1H), 2.16-2.12 (m, 2H), 1.78 (s, 3H), 1.71 (s, 3H), 1.43-1.38 (m, 2H), 1.17 (d, 3H, J=6.5 Hz).

Compounds (12-14) of Formula II were prepared generally as set forth in Scheme 3, using a substituted bromopyridine as R for purposes of illustration. Briefly, the 1,6-dienes compounds of Formula II were prepared by Grignard addition reaction from the corresponding Grignard reagents with appropriate aldehyde. The Grignard reagents were prepared from the corresponding aryl bromide. Then the coupled product was treated with POCl$_3$ to get the desired dienes.

Scheme 3

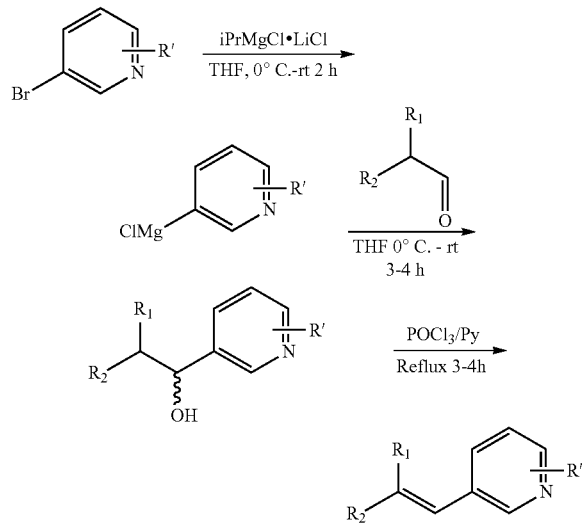

General/Typical Procedure for Grignard addition reaction: Isopropyl magnesium chloride.LiCl complex solutions was added to a solution of 4-Bromobenzene (5.6 g. 30 mmol) in THF at 0 C to make the corresponding Grignard reagent. 2,6-Dimethyl-5-heptenal (3.2 g, 22.5 mmol) was then added to a stirred solution of the Grignard reagent at 0° C. and allowed to reach room temperature and continue stirring additional 3 h. After stirring at room temperature for 3 h, the reaction is complete. The reaction mixture was then cooled down at 0° C. and quenched with ammonium chloride, extracted with ethyl acetate, washed with brine and dried over anhydrous Na$_2$SO$_4$, filtered and concentrated in rotary evaporator and purified by column chromatography to yield (4.5 g, 80%) of the coupled product as liquid.

General/Typical Procedure for dehydration reaction: The resulting coupled product (4.0 g, 16 mmol) was then treated with POCl$_3$ (3.7 g, 24 mmol) in pyridine (32 mL) solution and heated to reflux for 3 h. The reaction mixture was then cooled down and quenched with water, extracted with ethyl acetate, washed with brine and dried over anhydrous Na$_2$SO$_4$, filtered and concentrated in rotary evaporator and purified by column chromatography to yield (2.8 g, 75%) of the coupled product as liquid.

(E)-3-(3,7-Dimethylocta-1,6-dienyl) pyridine (12):
$^1$H-NMR (CDCl$_3$, 500 MHz): 8.57 (d, 1H, J=7 HZ), 8.53 (s, 1H), 7.571 (d, 1H, J=8 Hz), 7.27 (dd, 1H, J=7 & 8 Hz), 6.28 (d, 1H, J=16 Hz), 6.13 (dd, IH, J=8 & 16 Hz), 5.06-4.94 (m, 1H), 2.03-1.91 (m, 2H), 1.89-1.78 (m, 1H), 1.65 (s, 3H), 1.57 (s, 3H), 1.39-1.36 (m, 1H), 0.93 (d, 3H, J=7 Hz).
$^{13}$C-NMR (CDCl$_3$, 125 MHz): 149.80 (C), 149.70 (CH), 136.32 (CH), 135.41 (CH), 131.54 (C), 127.23 (C), 126.68 (CH), 124.40.41 (CH), 110.84 (CH), 37.28 (CH$_2$), 37.03 (CH$_2$), 26.02 (CH$_3$), 25.88 (CH$_3$), 20.74 (CH$_3$), 17.87 (CH).

Representative compounds 13 and 14 were synthesized according to the same protocol using appropriate staring materials. Overall yields varied from 40-50%.

(E)-2-(3,7-Dimethylocta-1,6-dienyl) pyridine (13)
$^1$H-NMR (CDCl$_3$, 500 MHz): 8.65 (d, 1H, J=7 HZ), 8.57-8.53 (m, 1H), 8.02 (d, 1H, J=9 Hz), 7.82 (dd, 1H, J=7 & 9 Hz), 6.42 (d, 1H, J=16 Hz), 7.19 (dd, IH, J=8 & 16 Hz), 5.10-5.04 (m, 1H), 2.23-2.10 (m, 1H), 2.09-1.89 (m, 2H), 1.64 (s, 3H), 1.58 (s, 3H), 1.39-1.36 (m, 2H), 0.95 (d, 3H, J=7 Hz).

(E)-5-(3,7-Dimethylocta-1,6-dienyl)-2-methoxypyridine (14)
$^1$H-NMR (CDCl$_3$, 500 MHz): 8.026 (s, 1H), 7.58 (d, 1H, J=10 Hz), 6.64 (d, 1H, J=9 Hz), 6.23 (d, 1H, J=16 Hz), 5.93 (dd, IH, J=15, 8 Hz), 5.09-5.06 (m, 1H), 3.89 (s, 3H), 2.27-2.24 (m, 1H), 1.98-1.94 (m, 2H), 1.65 (s, 3H), 1.57 (s, 3H), 1.39-1.36 (m, 2H), 1.04 (d, 3H, J=7 Hz).
$^{13}$C-NMR (CDCl$_3$, 125 MHz): 163.30 (C), 144.99 (CH), 136.32 (CH), 135.41 (CH), 131.54 (C), 127.23 (C), 126.68 (CH), 124.40.41 (CH), 110.84 (CH), 53.54 (CH$_3$), 37.28 (CH$_2$), 37.03 (CH$_2$), 26.02 (CH$_3$), 25.88 (CH$_3$), 20.74 (CH$_3$), 17.87 (CH).

Example 3: General and Specific Methods for the Synthesis of Compounds of Formula III Compounds of Formula III was prepared generally as set forth in Scheme 4, using a substituted benzylphosphonate as R for purposes of illustration. The phosphonate reagents were prepared from the corresponding benzyl bromide treated with triethyl phosphite following Arbuzov Reaction. Briefly, the 1,7-dienes compounds of Formula III were prepared by Wittig reaction from the corresponding phosphonate salt with appropriate ketone. Then the coupled olefin product was treated methyl magnesium iodide for demethylation reaction to get the desired phenol dienes.

Scheme 4

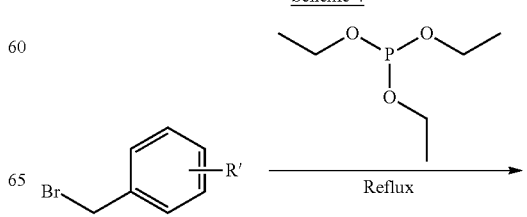

-continued

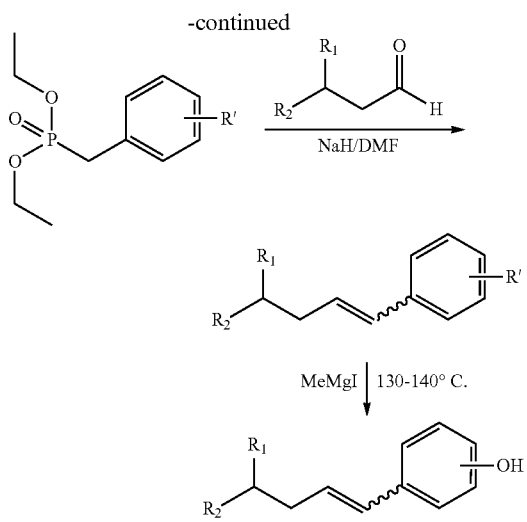

General/Typical Procedure for synthesis of phosphonate salt by Arbuzov Reaction: A solution of p-methoxybenzyl-bromide (10.5 g, 52.2 mmol) in P(OEt)$_3$ (25 mL) was refluxed for 5 h followed by removal of bromethane and excess triethylphosphite by distillation at reduced pressure. The residue provided 12.8 g (95%) of product was enough pure for next step.

General/Typical Procedure for Wittig reaction: To a solution of the phosphonium salt of benzyl bromide (5.2 g, 12 rnmol) and ketone in anhydrous DMF (25 mL), NaH was added at 0° C. portion wise. The reaction mixture was allowed to stir 0 C for 1 h, during which time the mixture developed a red color indicating the formation of ylide. After stirring at room temperature for 3 h, the reaction is complete. The mixture is diluted with water at 0 C and the product is extracted with EtOAc. The organic layer is washed with saturated aqueous NaHCO$_3$ and brine then dried over Na2SO$_4$. The solvent is removed under reduced pressure and the yellow residue was passed through a short bed of silica gel eluting with ethyl acetate-hexane (5:95) to yield the coupled product (3.6 g, 92%) in a ratio of (E/Z: 20/80) as a pale yellow oil.

General/Typical Procedure for demethylation reaction: To a solution of alkoxy diene (7 g, 21.8 mmol) in 10 ml of Et$_2$O was added a solution of MeMgI (3M) in Et$_2$O (10.0 ml, 30 mmol). The solvent was removed under reduced pressure, and the residue was heated under argon at 130-140° C. for 10 min. The mixture was cooled to rt, and the reaction was quenched with 10 ml of saturated aqueous NH$_4$Cl solution. The product was extracted with EtOAc (3×100 ml). The combined organic phase was washed with brine and dried over Na$_2$SO$_4$. The solvent was removed under reduced pressure, and the crude product was purified by careful column chromatography (silica gel; AcOEt/hexane 1:10) to afford the title compounds Z-isomer (2.6 g) and E-isomer 0.82 g respectively.

(Z)-5-(4,8-Dimethylnona-1,7-dienyl) benzene-1,3-diol (15):

$^1$H-NMR (CDCl$_3$, 500 MHz): 6.39 (d, 2H, J=2 Hz), 6.32 (d, 1H, J=2 Hz), 6.19 (d, IH, J=10 Hz), 5.63 (dt, IH, J=10 & 5 Hz), 5.31 (bs, 2H), 5.11-5.07 (m, 1H), 2.38-2.26 (m, 2H), 2.25-2.18 (m, 2H), 1.58 (s, 3H), 1.56 (s, 3H), 1.40-1.30 (m, 1H), 1.20-1.10 (m, 2H), 0.88 (d, 3H, J=7.5 Hz).

$^{13}$C-NMR (MeOD, 125 MHz): 157.09 (C), 156.70 (C), 132.86 (C), 130.85 (C), 129.04 (CH), 124.98 (CH), 108.67 (CH), 105.84 (CH), 101.66 (CH), 101.34 (CH), 40.59 (CH), 36.93 (CH$_2$), 36.03 (CH$_2$), 33.08 (CH$_2$), 25.94 (CH$_3$), 25.80 (CH$_3$), 19.72 (CH$_3$).

(E)-5-(4,8-Dimethylnona-1,7-dienyl) benzene-1,3-diol (16)

$^1$H-NMR (CDCl$_3$, 500 MHz): 6.41 (s, 2H), 6.31 (s, 1H), 6.23 (d, IH, J=16 Hz), 6.18 (dt, IH, J=16 & 5 Hz), 5.31 (bs, 2H), 5.13-5.09 (m, 1H), 2.41-2.26 (m, 2H), 2.25-2.18 (m, 2H), 1.58 (s, 3H), 1.56 (s, 3H), 1.44-1.38 (m, 1H), 1.18-1.07 (m, 2H), 0.98 (d, 3H, J=7.5 Hz)

The acid derivative, 17 was synthesized by O-alkylation reaction with ethyl bromoacetate followed by base catalyzed hydrolysis from the corresponding phenolic dienes 16.

Example 4: Tyrosinase Assay

Tyrosinase isolated from the mushroom species Agaricus bisporus was purchased from the Sigma-Aldrich Inc. (Cat #T3824-50KU). The enzyme was dissolved in the tyrosinase assay buffer (100 mM sodium phosphate, pH 6.8) to a concentration 10 U/μl, and stored at ~70° C. For the experiments the enzyme was freshly diluted in the assay buffer to a concentration of 0.2 U/μl. All test compounds were initially dissolved in 100% DMSO at a concentration of 400 mM. The compounds were further diluted to a concentration of 2 mM in 10% DMSO. 2 mM stock solutions of the compounds were then diluted two-fold in tyrosinase assay buffer with 10% DMSO to make ten total test concentrations. Tyrosinase substrate, L-DOPA (Sigma-Aldrich Inc, Cat #37830) was dissolved in the tyrosinase assay buffer to a concentration of 4 mM. This solution was then used as the four-fold concentrated stock of substrate in the tyrosinase activity assays. Tyrosinase assays were performed in clear-bottom 96-well plates at room temperature. The final volume of the assays was 200 μl per well. 100 μl of two-fold concentrated test compounds were mixed with 50 μl of 4 mM L-DOPA. The reactions were initiated by adding 50 μl of mushroom tyrosinase (0.2 U/l, 10 U per reaction), and allowed to proceed for 10 minutes. Accumulation of colored product was monitored by light absorption at 450 nm using a TECAN Genios plate reader. The assays were performed in duplicate and covered a concentration range of test compounds from 1 mM to 1.95 μM. Mean (n=2) absorption of wells containing no enzyme was subtracted as a blank. The data was computed as percentage activity of wells that contained the tyrosinase, but no test compounds.

Figure 9:
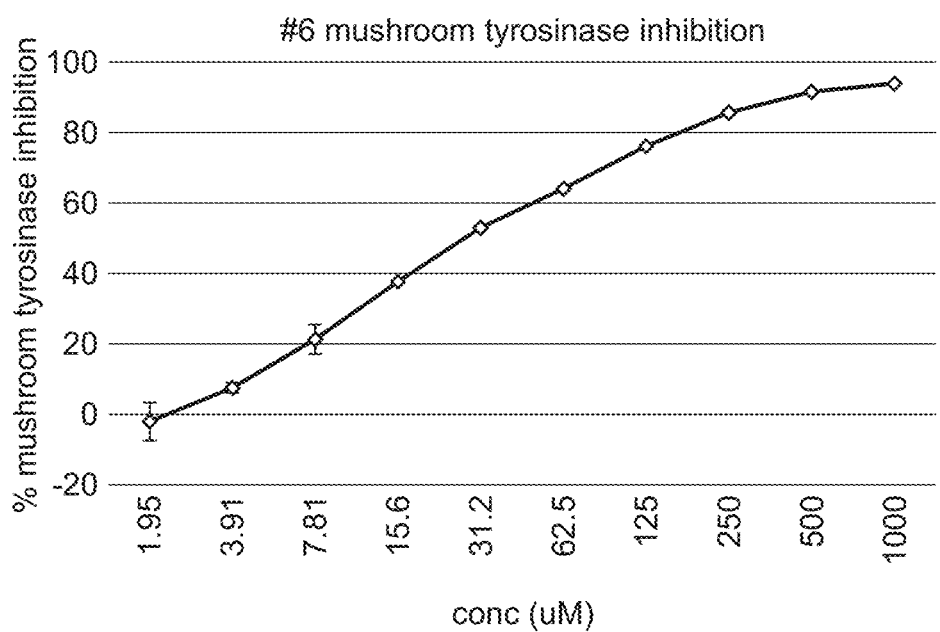
FIG. 9 graphically depicts the mushroom tyrosinase inhibition of compound 6 in an in vitro enzymatic inhibition assay as described in Example 4. There is defined dose-dependent inhibition of the tyrosinase enzyme by compound 6 with an $IC_{50}$ of 20 μM.

FIG. 9 graphically depicts the mushroom tyrosinase inhibition of compound 6 in an in vitro enzymatic inhibition assay as described in Example 4. There is defined dose-dependent inhibition of the tyrosinase enzyme by compound 6 with an IC$_{50}$ of 20 μM.

Example 5: Murine Melanoma Cell-Based Assays

Selected compounds were then tested for the ability to suppress melanin production by the murine melanoma cells B16-F1 as detailed below.

Murine melanoma cells B16-F1 were purchased from the ATCC (Cat #CRL-6323). Cell Titer96 AqueousOne Solution was purchased from Promega (Cat #G3582). 0.2 μm pore size, low protein binding filters were purchased from PALL Life Sciences. (Cat #PN4454). Alpha-MSH was purchased from the Sigma Aldrich (Cat #M4135-1MG). All tissue culture reagents were purchased from VWR (phenol-red-free DMEM, cat #12001-630, L-glutamine, cat #12001-698) and Fisher Scientific (Trypsin-EDTA, cat #25-200-056).

The B16-F1 cells were maintained in cell growth media (DMEM/High Glucose supplemented with glutamine, 10% fetal bovine serum, 50 units/ml penicillin, and 50 units/mL of streptomycin) at 37° C. in a humidified atmosphere of 95% air and 5% $CO_2$.

All test compounds were initially dissolved in 100% DMSO at a concentration of 400 mM. Then, 6 µL of 400 mM test compounds were added to 1.2 mL of the cell growth media giving a final concentration of 2 mM for the test compound and concentration of 0.5% for DMSO. The compounds were centrifuged for 1 h at 20,000×g. Supernatants (1 mL) were collected and filtered through sterile 0.2 µm filters. The compounds were serially diluted in two-fold increments in the sterile cell growth media supplemented with 0.5% DMSO, thus keeping the concentration of DMSO constant for all samples. These serially diluted compounds were subsequently used as two-fold concentrated stock solutions in the melanin production and cell viability assays. Equal volumes of 2× compounds were mixed with media containing 2 nM α-MSH to give a final concentration of 1 nM α-MSH, 0.5% DMSO, and 1× concentration of test compounds.

B16-F1 cells were seeded into the wells of clear-bottom 24-well plates at 50,000 cells per well, in 0.5 mL of cell growth media. On the following day, 0.5 mL of freshly prepared test compounds containing α-MSH were added to the wells. The cells were maintained at 37° C. in a humidified atmosphere of 95% air and 5% $CO_2$ for 48 hours. At the end of the incubation period, melanin-containing conditioned media was removed from the cells and transferred to another plate. To measure melanin content the light absorbance of conditioned media was taken at 492 nm using a TECAN Genios plate reader.

Viability of cells was measured using standard tetrazolium reduction assay based on redox potential of live cells. Cells were seeded in a clear-bottom 96-well plate in RPMI 1640 media with Glutamax (Fisher Scientific, cat #61870036) at a density of 5,000 cells/well. Cells were treated with test compounds dissolved in 100 µL RPMI 1640 media and incubated for 48 hours at 37° C. in a humidified atmosphere of 95% air and 5% $CO_2$. After incubation, 20 µL of Aqueous One Solution were added to each well and the plate was returned to the incubator for 30 minutes. Conversion of tetrazolium was monitored by measuring absorbance of cell wells at 492 nm using a TECAN Genios plate reader.

Results

The results of the representative experiments are summarized in FIGS. 2-8. More than 90% percent of the melanin produced by cultured melanoma cells is found in extracellular media. Therefore, at the end of the experiment melanin-containing media was collected and relative amounts of melanin were determined by absorption at 492 nm. Viability of cells was determined by a commonly used colorimetric procedure that is based on conversion of the tetrazolium compounds to colored formazan products (using Promega's CellTiter96 AqueousOne assay). Dehydrogenase enzymes in metabolically active cells accomplish this conversion, and the amount of formazan product is directly proportional to the number of living cells in culture. Mean (n=2) absorption of wells containing no cells was subtracted as blanks. The results were computed as percent of wells that contained the cells but no test compounds.

Example 6: Reconstructed Human Skin Studies
Materials and Methods

The skin whitening effects of test compounds were studied using a reconstructed skin model, Melanoderm™ provided by MatTek Corp. (Ashland, Mass.) according to the manufacturer's specifications. Briefly, normal human epidermal keratinocytes and normal human melanocytes derived from dark skin donors were co-cultured on a surface of collagen-coated membrane to form multi-layered, highly differentiated skin tissue (MEL-300-B). The tissues were maintained in the $CO_2$, incubator at 37° C. The apical surfaces of the reconstructed skin (9 mm in diameter) were exposed to air whereas the bottom surfaces remained in contact with 5 mL of maintenance medium, containing skin differentiating factors (EPI-100-NNM-113). Test compounds were formulated in 80% propylene glycol as follows: 10 mg of each test compound was dissolved in DMSO and diluted with 80% propylene glycol (1,2-propanediol, Sigma-Aldrich) to stock concentrations. The compounds were then sterilized by passing through 0.2 um filter and diluted in sterile water/propylene glycol to final test concentrations in 0.5% DMSO, 80% propylene glycol. In addition, the following controls were used: 80% propylene glycol with 0.5% DMSO, and 1% kojic acid in 80% propylene glycol.

'Test compounds were applied to the apical surface of the tissues as follows: 25 µl of each test compound, 25 µl of 80% propylene glycol (vehicle control), and 25 µl of 1% kojic acid (positive control). The samples were reapplied every other day for 14 days. All the samples were tested in duplicate. At the end of the experiment microscopic images were taken.

Results

The potential skin-whitening properties of test compounds were explored in a reconstructed skin model. The model consists of normal, human-derived epidermal keratinocytes and melanocytes, which have been co-cultured to form a multilayered, highly differentiated human epidermis. In this study the melanocytes were obtained from a highly pigmented donor.

Different concentrations of test compounds, 80% propylene glycol (the vehicle control), or 1% kojic acid (positive control) were repeatedly applied topically on the surface of the reconstructed skin for 15 days. Two of the test compounds, namely, compound #1, and compound #6 exhibited significant whitening effects on skin melanocytes, without causing any detectable alterations of cell morphology (FIG. 11B). Of them, compound #1 and #6 exhibited the greatest effect with significant whitening of melanocytes observed as early as 3 days after the beginning of the experiment (data not shown). Photographs of skin specimen taken after 15 days of the experiment show significant dose-dependent whitening effects on melanocytes, which appear on photographs as dark dendritic cells.

The compound #1 and #5 also exhibited the greatest effect on Propionibacterium (p-acnes) (MIC/MBC; <3.9 ppm) as well as inhibition of proinflammatory cytokines in low micro molar range.

Figure 10A:
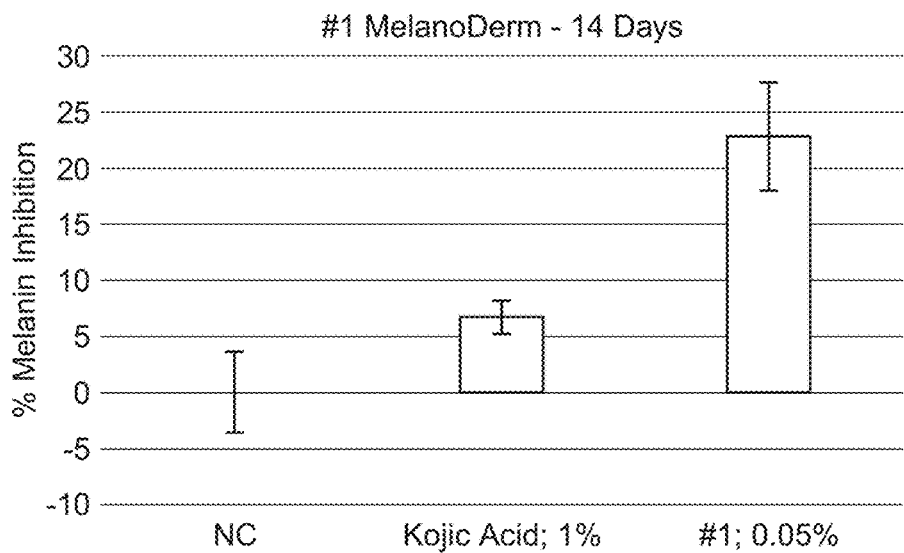
FIG. 10A depicts the melanin inhibition of compound 1 on reconstructed skin prepared as described in Example 6. The reconstructed skin was grown at the air-liquid interface, making it possible to mimic topical application of skin whitening agents. The reconstructed skin contained both keratinocytes and melanocytes.

FIG. 10A depicts the melanin inhibition of compound 1 on reconstructed skin prepared as described in Example 6. The reconstructed skin was grown at the air-liquid interface, making it possible to mimic topical application of skin whitening agents. The reconstructed skin contained both keratinocytes and melanocytes.

Figure 10B:
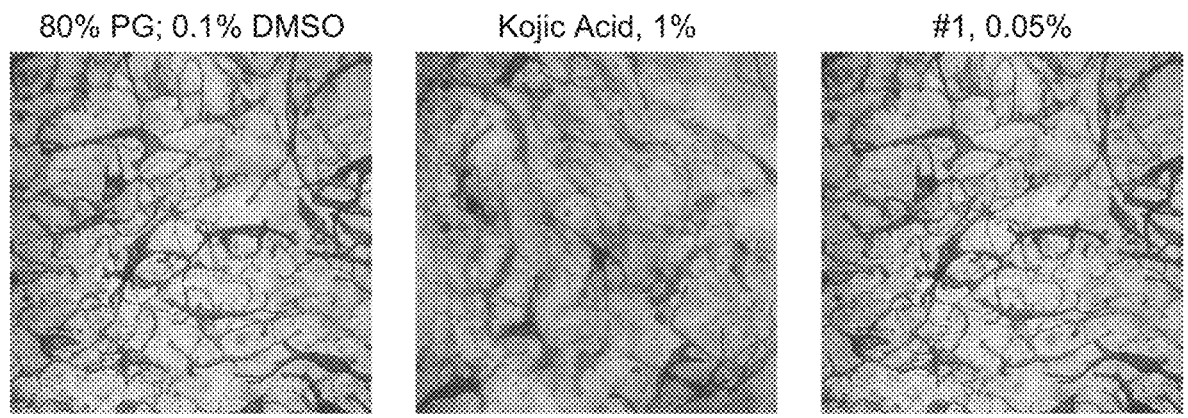
FIG. 10B depicts photographically the results of the reconstructed skin studies utilizing compound 1 as described in Example 6. Photographs of skin specimen taken after 14 days of the experiment show significant whitening effects on melanocytes, which appear on photographs as dark dendritic cells.

FIG. 10B depicts photographically the results of the reconstructed skin studies utilizing compound 1 as described in Example 6. Photographs of skin specimen taken after 14 days of the experiment show significant whitening effects on melanocytes, which appear on photographs as dark dendritic cells.

Figure 11A:
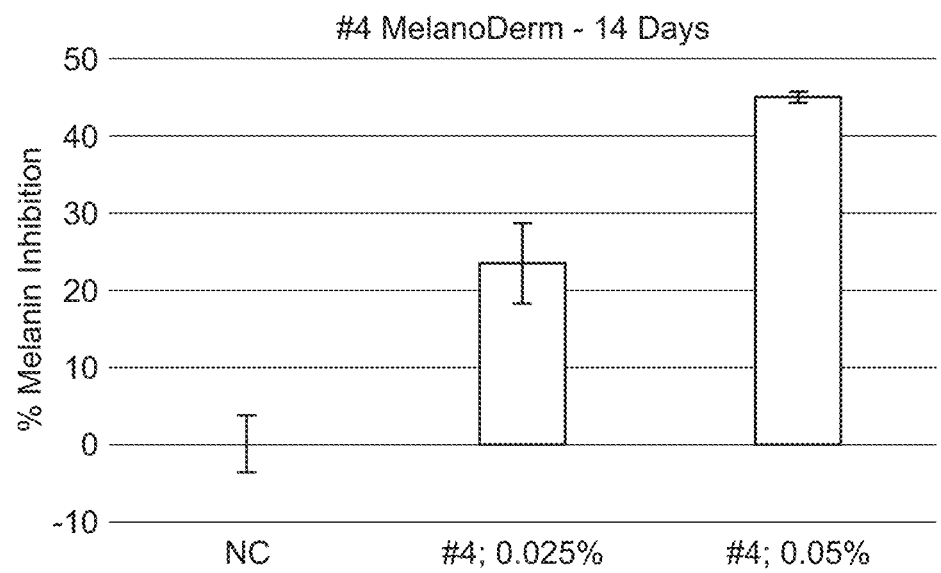
FIG. 11A depicts the melanin inhibition of compound 4 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 4 showed some toxicity.
Figure 11B:
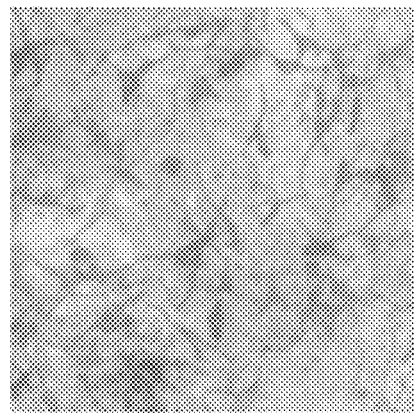
FIG. 11B depicts photographically the results of the reconstructed skin studies utilizing compound 4 as described in Example 6. Photographs of skin specimen taken after 14 days of the experiment show significant whitening effects on melanocytes, which appear on photographs as dark dendritic cells. At 0.05%, compound 4 showed some toxicity.
Figure 11B:
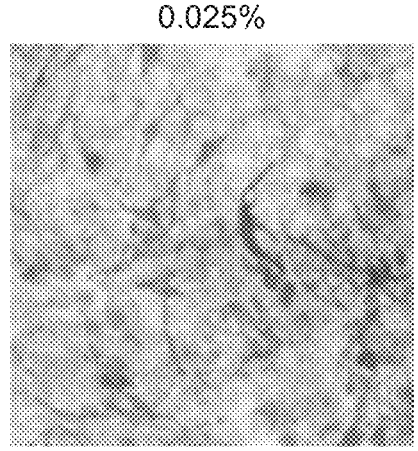
Figure 11B:
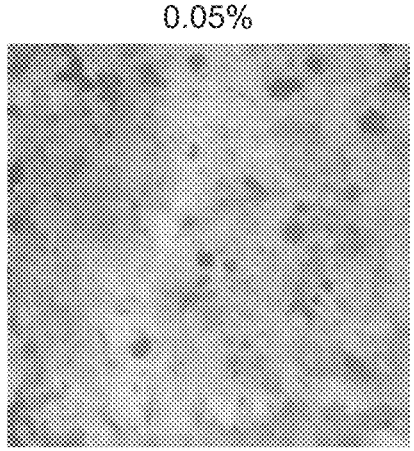

FIG. 11A depicts the melanin inhibition of compound 4 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 4 showed some toxicity.

FIG. 11B depicts photographically the results of the reconstructed skin studies utilizing compound 4 as described in Example 6. Photographs of skin specimen taken after 14 days of the experiment show significant whitening effects on melanocytes, which appear on photographs as dark dendritic cells. At 0.05%, compound 4 showed some toxicity.

Figure 12A:
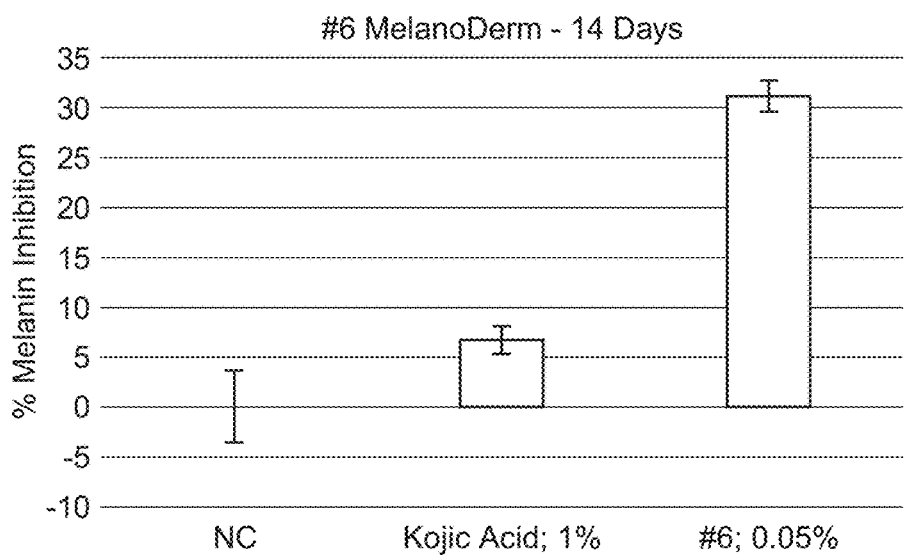
FIG. 12A depicts the melanin inhibition of compound 6 on reconstructed skin prepared as described in Example 6. The reconstructed skin was grown at the air-liquid interface, making it possible to mimic topical application of skin whitening agents. The reconstructed skin contained both keratinocytes and melanocytes.

FIG. 12A depicts the melanin inhibition of compound 6 on reconstructed skin prepared as described in Example 6. The reconstructed skin was grown at the air-liquid interface, making it possible to mimic topical application of skin whitening agents. The reconstructed skin contained both keratinocytes and melanocytes.

Figure 12B:
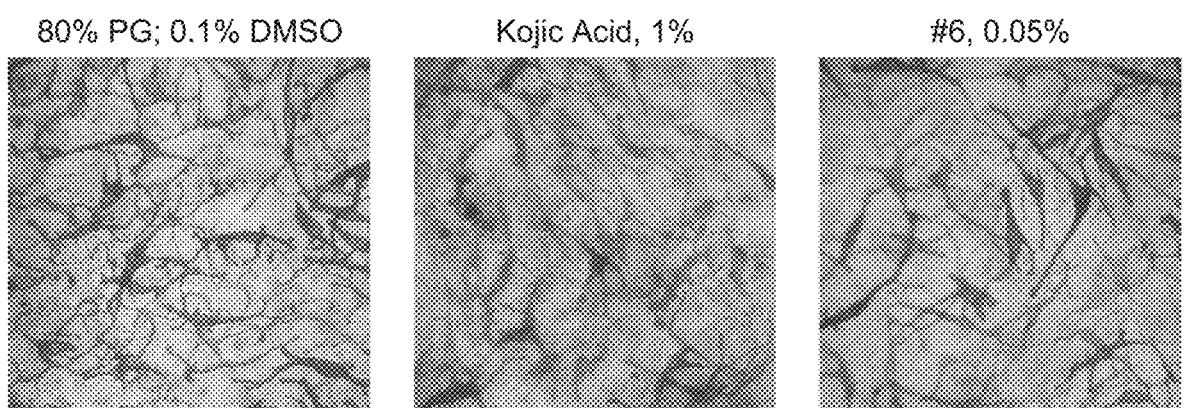
FIG. 12B depicts photographically the results of the reconstructed skin studies utilizing compound 6 as described in Example 6. Photographs of skin specimen taken after 14 days of the experiment show significant whitening effects on melanocytes, which appear on photographs as dark dendritic cells.

FIG. 12B depicts photographically the results of the reconstructed skin studies utilizing compound 6 as described in Example 6. Photographs of skin specimen taken after 14 days of the experiment show significant whitening effects on melanocytes, which appear on photographs as dark dendritic cells.

Figure 13A:
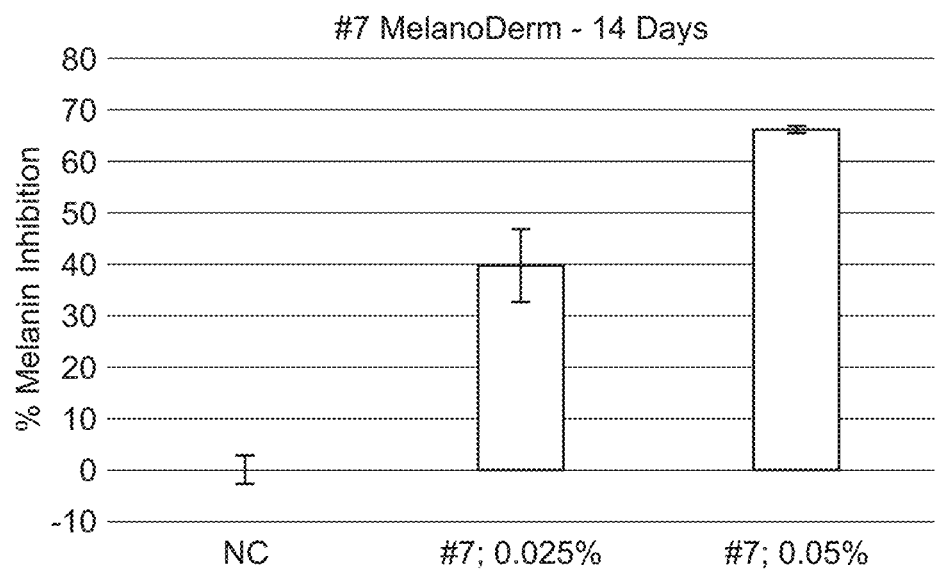
FIG. 13A depicts the melanin inhibition of compound 7 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 7 showed some toxicity.

FIG. 13A depicts the melanin inhibition of compound 7 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 7 showed some toxicity.

Figure 13B:
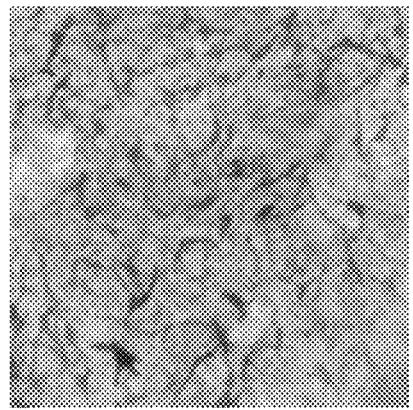
FIG. 13B depicts photographically the results of the reconstructed skin studies utilizing compound 7 as described in Example 6. Photographs of skin specimen taken after 14 days of the experiment show significant whitening effects on melanocytes, which appear on photographs as dark dendritic cells. At 0.05%, compound 7 showed some toxicity.
Figure 13B:
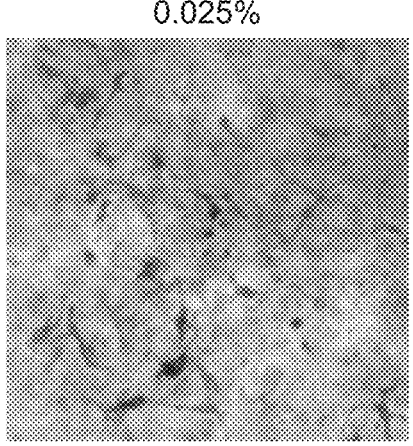
Figure 13B:
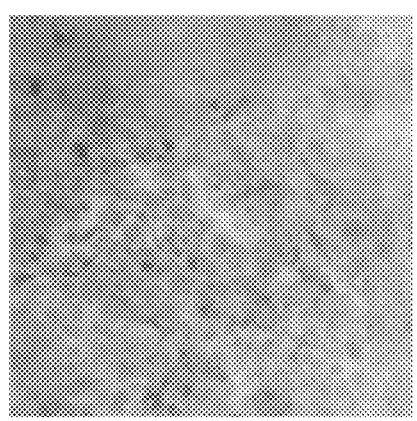

FIG. 13B depicts photographically the results of the reconstructed skin studies utilizing compound 7 as described in Example 6. Photographs of skin specimen taken after 14 days of the experiment show significant whitening effects on melanocytes, which appear on photographs as dark dendritic cells. At 0.05%, compound 7 showed some toxicity.

Figure 14:
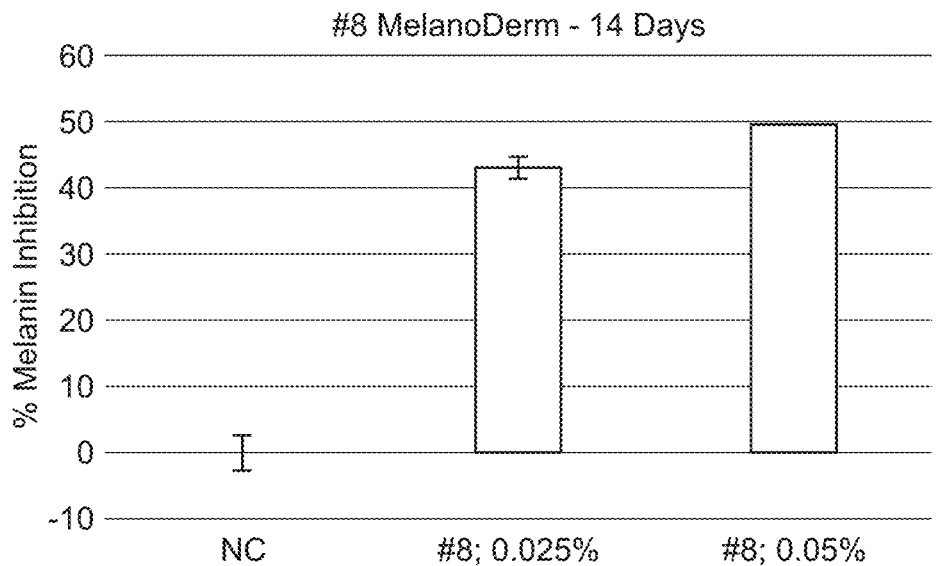
FIG. 14A depicts the melanin inhibition of compound 8 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 8 showed some toxicity.

FIG. 14A depicts the melanin inhibition of compound 8 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 8 showed some toxicity.

Figure 15A:
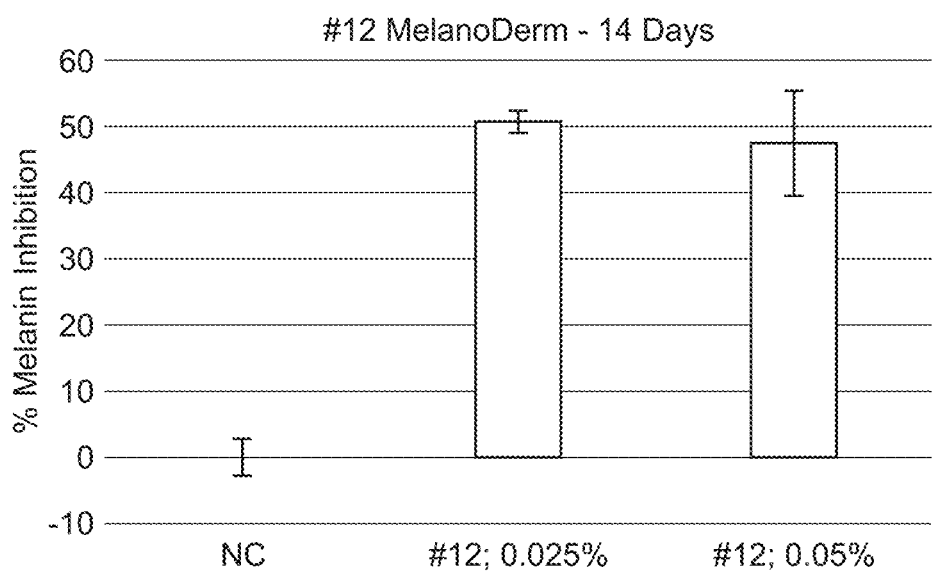
FIG. 15A depicts the melanin inhibition of compound 12 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 12 showed some toxicity.

FIG. 15A depicts the melanin inhibition of compound 12 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 12 showed some toxicity.

Figure 15B:
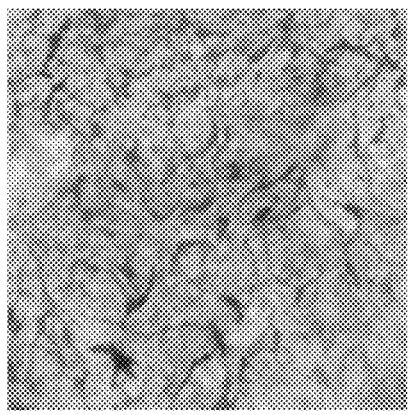
FIG. 15B depicts photographically the results of the reconstructed skin studies utilizing compound 12 as described in Example 6. Photographs of skin specimen taken after 14 days of the experiment show significant whitening effects on melanocytes, which appear on photographs as dark dendritic cells. At 0.05%, compound 12 showed some toxicity.
Figure 15B:
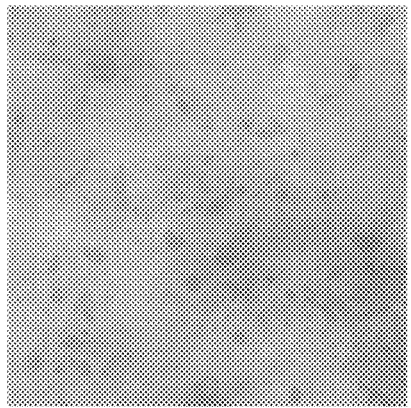

FIG. 15B depicts photographically the results of the reconstructed skin studies utilizing compound 12 as described in Example 6. Photographs of skin specimen taken after 14 days of the experiment show significant whitening effects on melanocytes, which appear on photographs as dark dendritic cells. At 0.05%, compound 12 showed some toxicity.

Figure 16A:
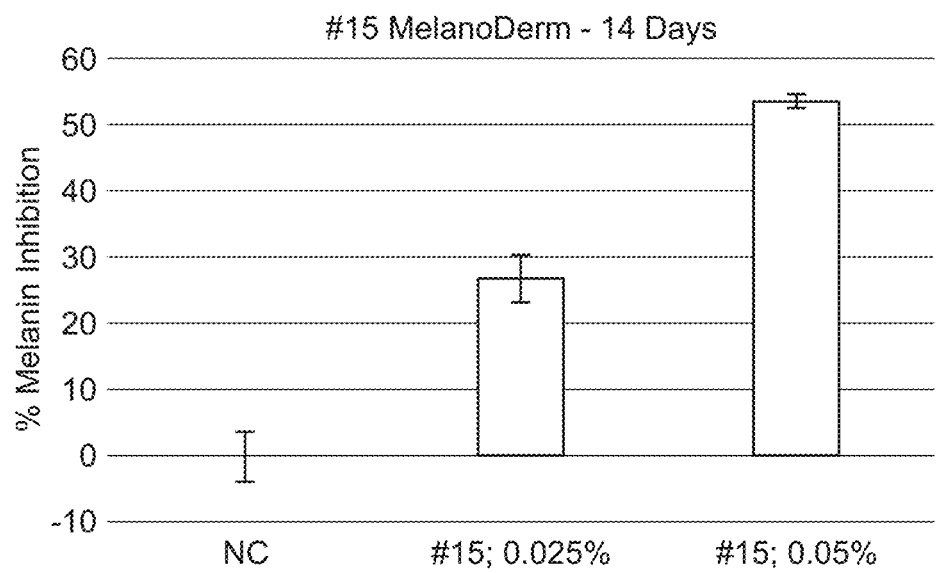
FIG. 16A depicts the melanin inhibition of compound 15 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 15 showed some toxicity.

FIG. 16A depicts the melanin inhibition of compound 15 on reconstructed skin prepared as described in Example 6. The reconstructed skin was grown at the air-liquid interface, making it possible to mimic topical application of skin whitening agents. The reconstructed skin contained both keratinocytes and melanocytes. At 0.05%, compound 15 showed some toxicity.

Figure 16B:
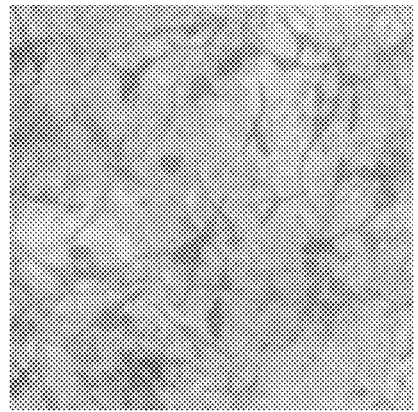
FIG. 16B depicts photographically the results of the reconstructed skin studies utilizing compound 15 as described in Example 6. Photographs of skin specimen taken after 14 days of the experiment show significant whitening effects on melanocytes, which appear on photographs as dark dendritic cells. At 0.05%, compound 15 showed some toxicity.
Figure 16B:
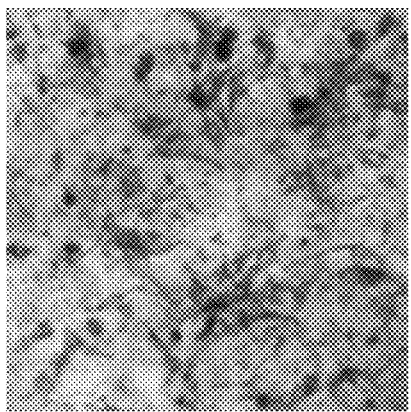
Figure 16B:
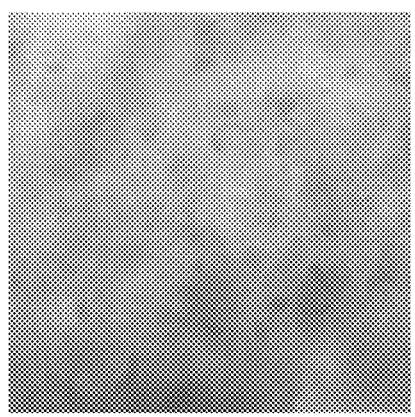

FIG. 16B depicts photographically the results of the reconstructed skin studies utilizing compound 15 as described in Example 6. Photographs of skin specimen taken after 14 days of the experiment show significant whitening effects on melanocytes, which appear on photographs as dark dendritic cells. At 0.05%, compound 15 showed some toxicity.

Example 7: P-Acne Test

The anti-microbial activity of the tested compounds were evaluated using published methods (Modugno e. al. (1994) Antimicrobial agents and Chemotherapy 38: 2362-2368; Misiek et. al. (1973) Antimicrobial agents and Chemotherapy 3: 40-48. *Propionibacterium* acnes (ATCC11827) was cultured for 20 hours at 37° C. in Reinforced Clostridal medium. The test article and positive control were dissolved in 1% DMSO with an incubation volume of 1 mL. The time of assessment was 1 day. Measurement of turbidity was used as the method of quantification. The compounds were tested in duplicate at concentrations of 250 ug/mL, 125 ug/mL, 62 ug/mL, 31 ug/mL, 16 ug/mL, 8 ug/mL, 4 ug/mL, 2 ug/mL relative to positive control ampicillin at 0.1 ug/mL.

Example 8: Inflammatory Test

Inhibition of COX-1 and COX-2 by tested compounds

In order to screen for compounds that inhibited COX-1 and Cox-2 activity, enzymatic inhibition assay kits were purchased from Cayman Chemical (cat #701050). Briefly, the compound being examined was treated against a fixed amount of COX-1 and COX-2 enzymes. A cleavable, peroxide chromophore was included in the assay to visualize the peroxidase activity of each enzyme in presence of arachidonic acid as cofactor. Typically, assays were performed in 96-well format. Each inhibitor, taken from a 1 M stock solution in 100% DMSO, was tested in duplicate at room temperature using the following range of concentrations: 1.9, 3.9, 7.8, 15.6, 31.2, 62.5, 125, 250, 500, and 1000 µM. To each well, 150 µL of Assay Buffer was added along with 10 µL of Hemin, 10 µL of inhibitor diluted in DMSO and 10 µL of either COX-1 or COX-2 enzyme. The compounds were incubated for 5 minutes at room temperature, followed by the addition of 20 µL of Colormietric Substrate solution and 20 µL of arachidonic acid solution to initiate the reaction. The plate was mixed and incubated for 2 minutes before reading the absorbance at 590 nm. The inhibitor concentration vs. % of inhibition was plotted and the $IC_{50}$ determined.

Inhibition of 5-Lipoxygenase Tested Compounds

One of the most important pathway involved in the inflammatory response is produced by non-heme, ion-containing lipoxygenases (5-LOX, 12-LOX and 15-LOX) which catalyze the oxidation of fatty acids such as AA to produce the hydroperoxides 5-, 12- and 15-HEPTE, which are then converted to leukotrienes. A Lipoxygenase Inhibition Assay was carried out using commercial kit from Cayman Chemical (cat #760700, 5-lipoxygenase from potato, cat #60400). The test article and positive control were dissolved in 1% DMSO. 90 µL of diluted potato lipoxygenase enzyme and 10 µL inhibitor were added to a flat-bottom clear 96-well microplate. The plate was pre-incubated for five minutes at room temperature. The reaction was initiated by the addition of 10 µL linoleic acid substrate. The plate was then placed on a shaker for 10 minutes at room temperature. 100 µL Chromogen solution was added to each well and the plate was shaken again for five minutes. The

The invention claimed is:

1. A compound of formula I:

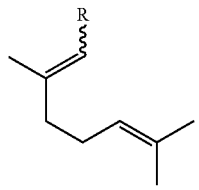

wherein R is selected from the group consisting of 1'-(4'-hydroxy)phenyl; 1'-(3'-hydroxy)phenyl; 1'-(2',4'-dihydroxy)phenyl; 1'-(3',5'-dihydroxy)phenyl with E and Z geometry.

2. A composition comprising (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

3. A method for inhibiting the production of melanin comprising administering to a subject in need thereof a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

4. A method for preventing and treating diseases and conditions related to the overproduction or uneven distribution of melanin comprising administering to a subject in need thereof an effective amount of a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

5. A method for whitening or lightening skin comprising administering to a subject in need thereof a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

6. A method for preventing melanin synthesis which is a symptom of a condition, disorder, or disease that is associated with tyrosinase inhibition, the method comprising administering to a subject in need thereof an effective amount of a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

7. A method for preventing melanin synthesis which is a symptom of a condition, disorder, or disease that is associated with non-tyrosinase inhibition, the method comprising administering to a subject in need thereof an effective amount of a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

8. A method for treating diseases and conditions caused by free radicals, oxidative stress, UV rays, or inflammation, the method comprising administering to a subject in need thereof an effective amount of a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

9. A method for inhibiting the browning and color changes in fruits, vegetables, juices and other food products comprising administering a composition comprising at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

10. The method of claim 6, wherein the condition, disorder, or disease is selected from the group consisting of suntan, hyper pigmentation spots caused by skin aging, melasma, liver diseases, thermal burns and topical wounds, skin pigmentation due to inflammatory conditions caused by fungal, microbial and viral infections, vitiligo, carcinoma, or melanoma.

11. A method for suppressing the activity of *Propionibacterium* (p-acnes) comprising administering to a patient in need thereof a composition comprising at least one the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

12. A method for deactivating the activity of proinflammatory cytokines, the method comprising administering to a patient in need thereof a composition consisting of at least one of the following compounds: (E/Z)-4-(2,6-dimethylhepta-1,5-dienyl)phenol (1); (E/Z)-3-(2,6-dimethylhepta-1,5-dienyl)phenol (2); (E/Z)-4-(2,6-dimethylhepta-1,5-dienyl)benzene-1,3-diol (3); (E/Z)-5-(2,6-dimethylhepta-1,5-dienyl)benzene-1,3-diol (4) or a pharmaceutically acceptable salt thereof.

13. The method of claim 8, wherein said diseases and conditions are selected from the group consisting of suntan, post inflammatory hyperpigmentation (PIH), hyper pigmentation spots caused by melasma, liver diseases, thermal burns and topical wounds, skin pigmentation due to inflammatory conditions caused by fungal, microbial and viral infections, vitiligo, carcinoma, or melanoma.

14. The method of claim 13, wherein the post inflammatory hyperpigmentation (PIH) is derived from acne, atopic dermatitis, allergic contact dermatitis, incontinent pigmentation, lichen planus, lupus erythematosus, morphea, mechanical trauma, ionizing or nonionizing radiation, burns, laser or drug therapies, skin infection or combinations thereof.

* * * * *